United States Patent
Hess et al.

(10) Patent No.: US 9,535,073 B2
(45) Date of Patent: Jan. 3, 2017

(54) PREDICTION AND RECOGNITION OF ACUTE KIDNEY INJURY AFTER SURGERY

(71) Applicant: Roche Diagnostics Operations, Inc., Indianapolis, IN (US)

(72) Inventors: Georg Hess, Mainz (DE); Andrea Horsch, Lucerne (CH); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/713,719

(22) Filed: Dec. 13, 2012

(65) Prior Publication Data

US 2013/0122530 A1    May 16, 2013

Related U.S. Application Data

(63) Continuation of application No. PCT/EP2011/059951, filed on Jun. 15, 2011.

(30) Foreign Application Priority Data

Jun. 15, 2010   (EP) .................................. 10165964

(51) Int. Cl.
*G01N 33/68* (2006.01)
*G01N 33/74* (2006.01)

(52) U.S. Cl.
CPC ...... *G01N 33/6872* (2013.01); *G01N 33/6893* (2013.01); *G01N 33/74* (2013.01); *G01N 2333/475* (2013.01); *G01N 2800/347* (2013.01)

(58) Field of Classification Search
CPC  G01N 33/6872; G01N 33/6893; G01N 33/74; G01N 2333/475; G01N 2800/347
See application file for complete search history.

(56) References Cited

U.S. PATENT DOCUMENTS

| | | | |
|---|---|---|---|
| 5,744,305 | A | 4/1998 | Fodor et al. |
| 2005/0158801 | A1* | 7/2005 | Hu et al. .................. 435/7.2 |
| 2007/0042424 | A1 | 2/2007 | Ebinuma et al. |
| 2010/0143951 | A1* | 6/2010 | Kronenberg et al. ........ 435/7.92 |
| 2010/0183520 | A1* | 7/2010 | Ramesh ..................... 424/9.2 |

FOREIGN PATENT DOCUMENTS

| | | | | |
|---|---|---|---|---|
| WO | 2008/084003 A1 | 7/2008 | | |
| WO | WO 2009038742 A2 * | 3/2009 | ............ | G01N 33/53 |
| WO | WO 2009040400 A1 * | 4/2009 | ............ | G01N 33/68 |
| WO | WO 2010025434 A1 * | 3/2010 | ............ | G01N 33/53 |
| WO | 2010/125165 A1 | 11/2010 | | |

OTHER PUBLICATIONS

Haase-Fielitz et al., Novel and conventional serum biomarkers predicting acute kidney injury in adult cardiac surgery—A prospective cohort study, Critical Care Medicine: 2009 vol. 37, No. 2, 553-560.*

Anderson, The Clinical Plasma Proteome: A Survey of Clinical Assays for Proteins in Plasma and Serum, Clinical Chemistry, 56:2, 177-185 (2010).*

Ahima, Rexford S., "Adipose Tissue as an Endocrine Organ," Obesity, Aug. 2006, pp. 242S-249S, vol. 14 Supplement.

Brincat, Stephen and Hilton, Rachel, "Prevention of acute kidney injury," British Journal of Hospital Medicine, Aug. 2008, pp. 450-454, vol. 69, No. 8.

Brown, Jeremiah R. et al., "Long-Term Survival After Cardiac Surgery is Predicted by Estimated Glomerular Filtration Rate," Annals of Thoracic and Cardiovascular Surgery, 2008, pp. 4-12, vol. 208.

Chan, Lawrence et al., "Human Liver Fatty Acid Binding Protein cDNA and Amino Acid Sequence," The Journal of Biological Chemistry, 1985, pp. 2629-2632, vol. 260, No. 5.

Han, Seung Hwan et al., "Adiponectin and Cardiovascular Disease," Journal of the American College of Cardiology, 2007, pp. 531-538, vol. 49, No. 5.

Hanley, James A. and McNeil, Barbara J., "The Meaning and Use of the Area under a Receiver Operating Characteristic (ROC) Curve," Radiology, Apr. 1982, pp. 29-36, vol. 143.

Kadowaki, Takashi et al., "Adiponectin and adiponectin receptors in insulin resistance, diabetes, and the metabolic syndrome," The Journal of Clinical Investigation, Jul. 2006, pp. 1784-1972, vol. 116, No. 7.

Kjeldsen, Lars et al., "Isolation and Primary Structure of NGAL, a Novel Protein Associated with Human Neutrophil Gelatinase," The Journal of Biological Chemistry, 1993, pp. 10425-10432, vol. 268, No. 14.

McIlroy, David R. et al., "Neutrophil Gelatinase-Associated Lipocalin and Acute Kidney Injury after Cardiac Surgery: The Effect of Baseline Renal Function on Diagnostic Performance," Clinical Journal of the American Society of Nephrology, 2010, pp. 211-219, vol. 5.

Mehta, Rajendra H. et al., "Bedside Tool for Predicting the Risk of Postoperative Dialysis in Patients Undergoing Cardiac Surgery," Circulation, 2006, pp. 2208-2216, vol. 114.

Needleman, Saul B. and Wunsch, Christian D., "A General Method Applicable to the Search for Similarities in the Amino Acid Sequence of Two Proteins," Journal of Molecular Biology, 1970, pp. 443-453, vol. 48.

Nolan, John P. and Sklar, Larry A., "Suspension array technology: evolution of the flat-array paradigm," Trends in Biotechnology, Jan. 2002, pp. 9-12, vol. 20, No. 1.

(Continued)

*Primary Examiner* — Andrea S Grossman
(74) *Attorney, Agent, or Firm* — Stinson Leonard Street LLP

(57) ABSTRACT

Systems, kits, and methods for predicting the risk of an adverse event related to acute kidney injury AKI as a consequence of a surgical intervention in a subject. Embodiments of the system and methods include means and steps for determining an amount of liver-type fatty acid binding protein (L-FABP) in a sample, such as a urine-sample of a subject; comparing the amounts of the L-FABP with a reference amount, and predicting the risk of an adverse event related to acute kidney injury as a consequence of surgical intervention in the subject.

2 Claims, 18 Drawing Sheets

(56) References Cited

OTHER PUBLICATIONS

Pearson, William R. and Lipman, David J., "Improved tools for biological sequence comparison," Proceedings of the National Academy of Sciences, Apr. 1988, pp. 2444-2448, vol. 85.
Smith, Temple F. and Waterman, Michael S., "Comparison of Biosequences," Advances in Applied Mathematics, 1981, pp. 482-489, vol. 2.
Song, Young Rim et al., "Prevention of Acute Kidney Injury by Erythropoientin in Patients Undergoing Coronary Artery Bypass Grafting: A Pilot Study," American Journal of Nephrology, 2009, pp. 253-260, vol. 30.
Wagener, Gebhard et al., "Association between Increases in Urinary Neutrophil Gelatinase-associated Lipocalin and Acute Renal Dysfunction after Adult Cardiac Surgery," Anesthesiology, 2006, pp. 485-491, vol. 105.
Yan, Li et al., The High Molecular Weight urinary Matrix Metalloproteinase (MMP) Activity Is a Complex of Gelatinase B/MMP-9 and Neutrophil Gelatinase-associated Lipocalin (NGAL), The Journal of Biological Chemistry, 2001, pp. 37258-37265, vol. 276, No. 40.
Bachorzewska-Gajewska, H. et al., "NGAL (neutrophil gelatinase-associated lipocalin) and L-FABP after percutaneous coronary interventions due to unstable angina in patients with normal serum creatinine," Advances in Medical Sciences, 2009, pp. 221-224, vol. 54, No. 2.
Devarajan, Prasad, "Emerging urinary biomarkers in the diagnosis of acute kidney injury," Expert Opinion in Medical Diagnostics, 2008, pp. 387-398, vol. 2, No. 4.

Ferguson, Michael A. et al., "Urinary liver-type fatty acid-binding protein predicts adverse outcomes in acute kidney injury," Kidney International, 2010, pp. 708-714, vol. 77.
Han, Won K. et al., "Urinary Biomarkers in the Early Detection of Acute Kidney Injury after Cardiac Surgery," Clinical Journal of the American Society of Nephrology, 2009, pp. 873-882, vol. 4.
Kamijo, Atsuko et al., "Urinary liver-type fatty acid binding protein as a useful biomarker in chronic kidney disease," Molecular and Cellular Biochemistry, 2006, pp. 175-182, vol. 284.
Kato, Koji et al., "Valuable Markers for Contrast-Induced Nephropathy in Patients Undergoing Cardiac Catheterization," Circulation Journal, 2008, pp. 1499-1505, vol. 72.
Liangos, Orfeas et al., "Comparative analysis of urinary biomarkers for early detection of acute kidney injury following cardiopulmonary bypass," Biomarkers, 2009, pp. 423-431, vol. 14, No. 6.
Malyszko, Jolanta et al., "Urinary and Serum Biomarkers after Cardiac Catheterization in Diabetic Patients with Stable Angina and without Severe Chronic Kidney Disease," Renal Failure, 2009, pp. 910-919, vol. 31.
Nakamura, Tsukasa et al., "Urinary Excretion of Liver-Type Fatty Acid-Binding Protein in Contrast Medium-Induced Nephropathy," American Journal of Kidney Disease, 2008, pp. 439-444, vol. 47.
Negishi, Kousuke et al., "Monitoring of Urinary L-Type Fatty Acid-Binding Protein Predicts Histological Severity of Acute Kidney Injury," The American Journal of Pathology, Apr. 2009, pp. 1154-1159, vol. 174, No. 4.
Portilla, D. et al., "Liver fatty acid-binding protein as a biomarker of acute kidney injury after cardiac surgery," Kidney International, 2008, pp. 465-472, vol. 73.

\* cited by examiner

PREDICTION AND RECOGNITION OF ACUTE KIDNEY INJURY AFTER SURGERY

CROSS-REFERENCE TO RELATED APPLICATIONS

This application is a continuation of International Application No. PCT/EP2011/059951, filed Jun. 15, 2011 which claims the benefit of European Patent Application No. 10165964.7, filed Jun. 15, 2010, the disclosures of which are hereby incorporated by reference in their entirety.

BACKGROUND OF THE DISCLOSURE

Acute kidney injury represents a significant problem in clinical medicine. Five percent of hospitalized patients and up to 30 percent of patients in intensive care units will develop acute kidney injury ("AKI"). In AKI, serum creatinine levels rise slowly and it may take 2-3 days before kidney injury becomes apparent, in general indicated by an increase in creatinine of at least 0.3 mg/dl or an increase of more than 50 percent from baseline (Devarajan, Expert Opinion Med Diagn 2008, 2: 387-398).

The pathogenesis of postoperative AKI appears multifactorial, and its association with increased morbidity and long term mortality is well established (Brown et al Ann Thorac Surg 2008, 86: 4-11).

Coronary bypass surgery is preferentially carried out in patients in whom percutaneous coronary intervention is not possible due to the localization or extent of coronary atherosclerosis. This intervention is associated with a significant risk of AKI, this risk has been described to range between 10 and 20%, and wherein 1 to 5 percent of these individuals require dialysis (Mehta, Circulation 2006: 114 2208-16).

AKI may be prevented in patients who are known to be at increased risk by maintaining a careful fluid balance during surgery and, avoiding other precipitating factors of AKI, such as discontinuation of ACE inhibitors, NSAIDs and other drugs known to cause kidney injury before surgery, and the careful use of diuretics, specifically loop diuretics. Details are summarized in Brit J. of Hospital Medicine, 2008, 69, 450-454 (for details see Tables 2 and 3).

It is important to recognize early evidence of acute kidney injury in particular in low risk population which is frequently subject to early discharge. Although many cases are reversible if diagnosed and treated early, the overall survival rate remains about 50 percent because many patients with AKI have significant underlying disorders, e.g. sepsis, respiratory failure. Frequently death is caused by these disorders, rather than by the renal failure itself. In about 10 percent of the cases dialysis or transplant is required, either as an immediate treatment or as renal function slowly deteriorates. AKI can be fully reversible if treated appropriately and in time. As mentioned above, renal function may also deteriorate to chronic renal failure. Treatment may include immediate treatment of pulmonary edema and hyperkalemia; dialysis; adjustment of drug regimen, restriction of water, Na, and K intake, phosphate binders and Na polystyrene sulfonate.

BRIEF SUMMARY OF THE DISCLOSURE

The instant disclosure provides methods and means for predicting risk of an individual to suffer from AKI after a surgical intervention, such as a cardiac intervention (including, for example, a coronary bypass surgery). The instant disclosure also provides means to predict the risk of an individual to suffer from AKI after a surgical intervention based on analysis of a sample obtained before carrying out the surgical intervention.

The present disclosure relates to diagnostic methods and means. More specifically, it relates to a method for predicting the risk of acute kidney injury (AKI) in individuals who will receive a surgical intervention, such as a cardiac intervention, for example coronary bypass surgery. The present disclosure, likewise, relates to a method for predicting the risk of acute kidney injury in individuals having undergone a surgical intervention, such as cardiac intervention, for example coronary bypass surgery, and to a method of diagnosing acute kidney injury in patients having undergone a surgical intervention, such as cardiac intervention, for example coronary bypass surgery. Moreover, the present disclosure relates to devices, kits for carrying out said method and a method of deciding on a suitable therapy in patients suffering from AKI after a surgical intervention.

According to some embodiments, the present disclosure relates to a method for predicting the risk of a subject to experience an adverse event related to acute kidney injury AKI after a surgical intervention in a subject, based on the comparison of the amounts of liver-type fatty acid binding protein (L-FABP) or a variant thereof, determined in a urine sample of the subject, also referred to as urinary liver-type fatty acid binding protein, determined in a sample of said subject, to at least one reference amount.

According to some embodiments, the method of the present disclosure comprises at least one of the following steps and/or may comprise the following steps: a) determining the amounts of liver-type fatty acid binding protein (L-FABP) or a variant thereof, for example urinary liver-type fatty acid binding protein (L-FABP), in sample, such as a urine-sample of a subject; b) comparing the amounts determined in step a) with reference amounts; c) predicting the risk based on the comparison carried out in step b).

In some embodiments the present disclosure provides a method for predicting the risk of a subject to experience adverse event related to acute kidney injury AKI after a surgical intervention in a subject, comprising the steps of: a) determining the amounts of liver-type fatty acid binding protein (L-FABP) or a variant thereof, for example urinary liver-type fatty acid binding protein (L-FABP) or a variant thereof, in a sample, for example a urine-sample of a subject; b) comparing the amounts determined in step a) with reference amounts; and c) predicting the risk based on the comparison carried out in step b).

In another embodiment of the present disclosure, the present disclosure provides a method for predicting the risk of a subject to experience adverse event related to acute kidney injury AKI after a surgical intervention in a subject, comprising the steps of: a) determining the amounts of liver-type fatty acid binding protein (L-FABP) or a variant thereof, for example urinary liver-type fatty acid binding protein (L-FABP) or a variant thereof, in a sample, such as a urine-sample of a subject; and b) comparing the amounts determined in step a) with reference amounts; whereby the risk of the subject to experience adverse event related to acute kidney injury AKI after a surgical intervention is predicted.

In some embodiments of the present disclosure, the amount of adiponectin or a variant thereof or a variant thereof is determined in the sample, such as the urine sample, further to the amount of L-FABP or a variant thereof, and the risk is predicted based on the comparison of the marker amounts with reference amounts In further embodiments of the present disclosure, the amount of at least one further marker selected from albumin or a variant thereof and neutrophil gelatinase associated lipocalin (NGAL) or a variant thereof is measured in the urine sample, and the risk is predicted based on the comparison of the marker amounts with reference amounts. In such embodiments, the amount of only one additional marker from the above-cited group (further to L-FABP or a variant thereof) and, in some embodiments adiponectin or a variant thereof, will be measured, or the amounts of both additional markers further to L-FABP or a variant thereof and adiponectin or a variant thereof.

In some embodiments, the risk is predicted prior to the surgical intervention. The present disclosure also includes embodiments in which the risk is predicted following surgical intervention.

Moreover, the present disclosure relates to a method of deciding on a suitable therapy in a subject patient as defined beforehand, a method of monitoring the therapy, and a device and a kit for carrying out the methods of the present disclosure.

According to some embodiments, a method of diagnosing acute kidney injury in a subject is provided. Embodiments of the instant method include the steps of determining an amount of liver-type fatty acid binding protein, or a variant thereof, in a portion of a sample of a subject, comparing the amount of liver-type fatty acid binding protein, or variant thereof, determined in said step of determining to a liver-type fatty acid binding protein reference amount, and providing a diagnosis of acute kidney injury in the subject if the amount of liver-type fatty acid binding protein, or the variant thereof, determined in said step of determining is greater than the liver-type fatty acid binding protein reference amount.

According to some embodiments of the instant methods, the step of determining comprises contacting, in vitro, the portion of the sample with an antibody having specific binding affinity for liver-type fatty acid binding protein, or a variant thereof. In some such embodiments, the liver-type fatty acid binding protein reference amount is 10.7 µg/g creatinine.

Some embodiments of the disclosed methods include the sample being a urine sample. In some further embodiments, the sample of the subject is provided prior to a surgical intervention.

According to other embodiments of the instant disclosure, a method of diagnosing a subject as at increased risk of for an adverse event related to acute kidney injury after a surgical intervention is provided. In some embodiments, the method includes the steps of a) determining an amount of liver-type fatty acid binding protein, or a variant thereof, in a portion of a sample of a subject, the sample obtained from the subject prior to a surgical intervention; b) comparing the amount of liver-type fatty acid binding protein, or the variant thereof, determined in said step of determining to a liver-type fatty acid binding protein reference amount; and c) providing a diagnosis of at increased risk for an adverse event related to acute kidney injury after the surgical intervention if the amount of liver-type fatty acid binding protein, or the variant thereof, determined in said step of determining is greater than the liver-type fatty acid binding protein reference amount.

According to yet further embodiments of the instant disclosure, a device adapted for diagnosing a subject as at increased risk of for an adverse event related to acute kidney injury after a surgical intervention is provided. According to some embodiments, the device includes means for determining an amount of liver-type fatty acid binding protein, or a variant thereof, in a sample from the subject; means for comparing the determined amount of liver-type fatty acid binding protein, or the variant thereof, to a liver-type fatty acid binding protein reference amount; and means for providing a diagnosis of at increased risk for an adverse event related to acute kidney injury after a surgical intervention if the amount of liver-type fatty acid binding protein, or the variant thereof, determined in the sample of the subject is greater than the liver-type fatty acid binding protein reference amount.

In some embodiments, the device includes means for determining an amount of adiponectin, or a variant thereof, in a sample from the subject, and means for comparing the determined amount of adiponectin, or the variant thereof, to an adiponectin reference amount. In such embodiments, the means for providing a diagnosis further comprise means for providing a diagnosis of at increased risk for an adverse event related to acute kidney injury after the surgical intervention if the amount of adiponectin, or variant thereof, determined in the sample of the subject is greater than the adiponectin reference amount.

According to even more embodiments of the device, the means for comparing comprises executable implemented rules. In some such embodiments, the executable implemented rules are executed by a processor of a computing device. In even further embodiments, the liver-type fatty acid binding protein reference amount is a stored value.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

Figure 1:
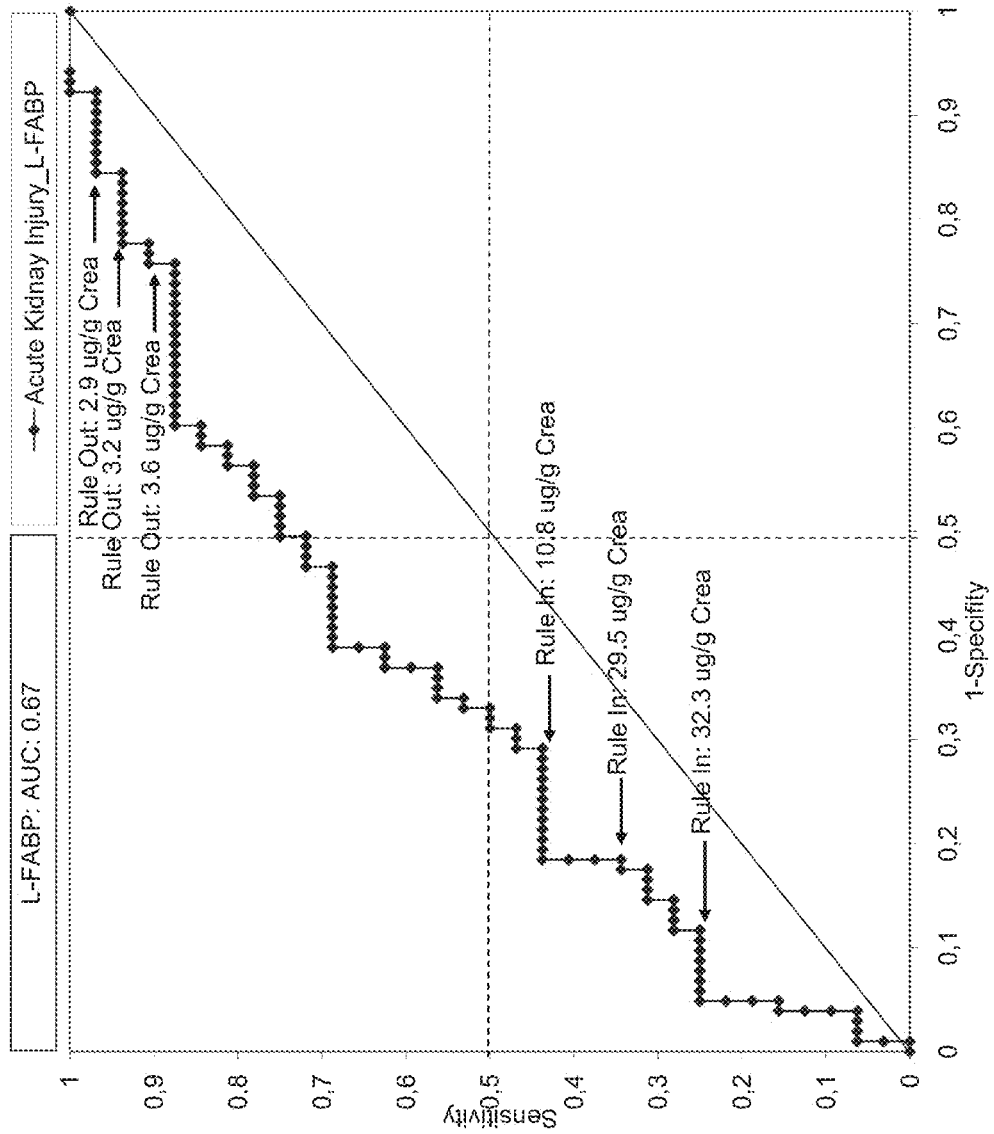
FIG. 1 is a receiver operating characteristic ("ROC") analysis for urinary L FABP of samples obtained from the patients described in Example 1 before surgery in which analysis was performed with respect to the clinical endpoint acute kidney injury (yes or no).

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Methods of the present disclosure include in vitro methods. Moreover, they may comprise steps in addition to those explicitly mentioned above where appropriate. For example, further steps may relate to sample pre-treatments or evaluation of the results obtained by the method.

The amounts of the markers determined in the context of the present disclosure (i.e. L-FABP or a variant thereof and optionally, adiponectin or a variant thereof and, optionally, albumin or a variant thereof, and, optionally, NGAL or a variant thereof may be determined in a urine sample of the respective subject. As the case may be, the marker(s) may also be determined in a blood, plasma or serum sample of the respective subject.

The term "adverse event related to acute kidney injury AKI" which may be used interchangeably with the term "acute kidney injury AKI related adverse event" refers to events/complications which are known to the person skilled in the art to occur in individuals suffering from AKI. The term may also include AKI itself, need for dialysis and death. In the context of patients undergoing surgery, acute kidney injury is defined as an increase in creatinine of at least 0.3 mg/dl within 3 days. Because of the delay in increase of creatinine this final diagnosis is frequently made late. Early signs of impaired kidney function are the reduction in urine volume. Intravasal hypovolemia may mimic acute kidney injury, in this case application of fluids results in rapid restoration of diuresis. In case oliguria proceeds to anuria (no or little urine excretion) and depending on the duration of anuria, intravasal volume overload occurs which may be associated with the clinical signs of heart failure specifically in individuals with pre-existing cardiac dysfunction. In case diuretics and fluid restriction are ineffective, dialysis is required. There are no clear recommendations for the initiation of dialysis, however blood urea concentrations above 100 mg/dl, hyperkalemia or acidosis are used for a decision to initiate dialysis. Decision making may be supported by chest X ray, echocardiography, ultrasound and possibly CT scan if needed.

The terms "predicting" and "predicting the risk" as used herein refers to assessing the probability according to which a subject will suffer from an AKI related adverse event in the future, e.g., AKI, need for dialysis and/or death. According to embodiments, the prediction is based on the analysis of a patient sample prior to the surgical intervention being carried out. As will be understood by those skilled in the art, such an assessment is usually not intended to be correct for 100% of the subjects to be diagnosed. The term, however, requires that a statistically significant portion of subjects can be diagnosed to suffer from the said disease (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. According to embodiments of the instant disclosure, confidence intervals are generally at least 90%, at least 95%, at least 97%, at least 98% or at least 99%. Also, the p-values are generally 0.1, 0.05, 0.01, 0.005, or 0.0001.

In general, an adverse event as specified elsewhere in the application occurs within 3 days, e.g. 1 day, or 2 days, or 3 days, for example 3 days, as determined by creatinine or GFR.

"Monitoring" as used herein relates to keeping track of the pathophysiological state of the respective individual relative to AKI related events, in particular AKI itself or need for dialysis, occurrence and/or progression of the disease or the influence of a particular treatment on the progression of disease. Diagnosing as used herein refers to analyzing and monitoring of the relevant disease. In particular, diagnosing means analyzing the pathology of specific parts of an organ (e.g. glomerules, tubules and henle loops of the kidney) and estimating the extent of damage and repair (e.g. in case of the tubules).

The term "subject" as used herein relates to animals, such as mammals, and humans. According to embodiments of the present disclosure, the subject may be apparently healthy, in particular with respect to kidney function (based on the glomerular filtration rate (GFR) and/or serum creatinine). A GFR of ≥about 60 ml/min/1.73 m$^2$ (i.e. filtration rate per 1.73 m$^2$ of body surface) is considered, within in the context of the present disclosure, to indicate an apparently healthy subject. A serum creatinine value of ≤1.3, preferably ≤1.2 mg/dl is considered to indicate, within the context of the present disclosure, an apparently healthy subject. The limit of the serum creatinine value quoted above in general corresponds to the upper limit of normal of the test method.

In the context of the present disclosure, the term "apparently healthy" is known to the person skilled in the art and refers to a subject which does not show obvious signs of an underlying disease. The disease here is related to an impaired kidney function, in particular in respect to GFR, for example based on creatinine clearance, in particular its upper limit as specified above. The subject, thus, may suffer from an impaired kidney function as defined below, but generally does not show obvious signs such that the impaired kidney function can be diagnosed or assessed without detailed diagnostic examination by a physician. In particular, the diagnosis by a specialist (e.g. a nephrologist) would be required to diagnose impaired kidney function in the apparently healthy subject not showing obvious symptoms of the disease. The term "impaired kidney function" may also be referred to as "renal disorder", in the context of the present disclosure. One example for a renal disorder is "renal failure".

The term "kidney function" as used herein is well known to the person skilled in the art. It may be used interchangeably with "renal function" and relates to the capacity of the kidney for urine production, control and elimination of body water and body fluids, and homeostasis and filtration of electrolytes and wastes, and, frequently, erythropoietin synthesis.

One of the first hints for impaired kidney function (renal failure) as used in the present application is the presence of protein in urine (micro- or macroalbuminuria).

In renal failure, kidney function is not adequate, resulting in decreased urine production, accumulation of body water and body fluids disturbances, and accumulation of electrolytes and wastes which are removed by filtration in healthy kidneys. Moreover, anemia is frequently observed as a consequence of diminished erythropoietin synthesis.

Kidney function is evaluated using values calculated from formulae based on results of blood and urine tests, in general GFR (the volume of blood filtered through the kidney per minute) and/or creatinine clearance.

GFR is one of the best overall measures of kidney function expressed in mL/min. Normal GFR in young, healthy adults is about 120 to 130 mL/min/1.73 m$^2$ and declines with age to about 75 mL/min/1.73 m$^2$ at age 70. Chronic kidney disease is defined by a GFR<60 mL/min/1.73 m$^2$ for >3 mo. Currently considered the gold standard for GFR measurement is inulin clearance. Inulin is neither absorbed nor secreted by the renal tubule and therefore it is the ideal marker for evaluation of kidney function. However, its measurement is cumbersome and therefore it is mostly used in research settings.

Creatinine is produced at a constant rate by muscle metabolism and is freely filtered by the glomeruli and also is secreted by the renal tubule. Because creatinine is secreted, creatinine clearance (CrCl) overestimates GFR by about 10 to 20% in people with normal kidney function and up to 50% in those with advanced renal failure.

Because serum creatinine by itself is inadequate for evaluation of kidney function, several formulae have been devised to estimate CrCl using serum creatinine and other factors. The Cockcroft and Gault formula can be used to estimate CrCl. It uses age, lean body weight, and serum creatinine level. It is based on the premise that daily creatinine production is 28 mg/kg/day with a decrease of 0.2 mg/yr of age.

Acute kidney injury (AKI), as well as chronic kidney disease (CKD) are known to the person skilled in the art and generally recognized as referring to renal failure as determined by GFR or creatinine clearance.

CKD is known as a loss of renal function which may worsen over a period of months or even years. The symptoms of worsening renal function are unspecific. In CKD glomerular filtration rate is significantly reduced, resulting in a decreased capability of the kidneys to excrete waste products by water and solute filtration. Creatinine levels may be normal in the early stages of CKD. CKD is not reversible. The severity of CKD is classified in five stages, with stage 1 being the mildest and usually causing few symptoms. Stage 5 constitutes a severe illness including poor life expectancy and is also referred to as end-stage renal disease (ESRD), chronic kidney failure (CKF) or chronic renal failure (CRF).

Acute kidney injury (AKI), previously also referred to as acute renal failure (ARF), is a rapid loss of kidney function which may originate from various reasons, including shock, low blood volume, exposure to nephrotoxic compounds and urine congestion following urethra obstruction. Contrary to CKD, AKI may be reversible. AKI is diagnosed on the basis of creatinine levels, urinary indices like blood urea nitrogen (BUN), occurrence of urinary sediment, but also on clinical history. A progressive daily rise in serum creatinine is considered diagnostic of AKI.

AKI is characterized by a rapid decline in glomerular filtration rate over hours to days, in particular of at least 0.3 mg/dl within 3 days.

AKI is heterogeneous in terms of its underlying causes, comprising causes occurring in the setting of renal hypoperfusion (prerenal), causes occurring in predominant compartments of the kidney (intrinsic or renal), and causes related to urinary tract obstruction (postrenal).

Prerenal causes of AKI are those that decrease effective blood flow to the kidney. These include systemic causes, such as low blood volume, low blood pressure, and heart failure, as well as local changes to the blood vessels supplying the kidney. The latter include renal artery stenosis (narrowing of the renal artery) and renal vein thrombosis (formation of blood clots in the renal vein). To be more precise, prerenal causes include hypovolemia such as severe hemorrhage, gastrointestinal fluid loss (e.g. caused by diarrhea), renal fluid loss (e.g. caused by diuretics), extravascular sequestration (e.g. caused by burns or severe hypalbuminemia), or decreased intake (e.g. dehydration). Also altered hemodynamics may be the cause of prerenal acute renal failure, this includes low cardiac output, systemic vasodilatation, renal vasoconstriction, impairment of renal autoregulatory responses or hepatorenal syndrome.

Intrinsic or renal causes of AKI are those occurring in the kidney itself and include damage to the glomeruli, renal tubules, or interstitium which are each caused by glomerulonephritis, acute tubular necrosis (ATN), and acute interstitial nephritis (AIN), respectively. To be more precise, intrinsic or renal causes include renal artery obstruction, diseases of the glomeruli or vasculature, acute tubular necrosis (which includes infections but also drugs such as radiocontrast agents, antibiotics and chemotherapy) interstitial nephritis and intratubular obstruction.

Postrenal causes of AKI comprise urinary tract obstruction (of the ureter, the urethra and/or the bladder neck). This may be related to benign prostatic hyperplasia, kidney stones, or an obstructed urinary catheter.

Early clinical sign of AKI is oliguria with a decreased urine output of less than 400 ml/day associated with extracellular fluid overload. Electrolyte- and acid/base abnormalities can also be found, this in finally followed by an increase of urea and creatinine. While postrenal causes of acute renal failure can be diagnosed by imaging and specifically by ultrasound, prerenal and intrinsic causes of acute renal failure cannot be diagnosed using imaging techniques.

In the context of the present disclosure, the term "tubular damage" refers to epithelial injury in tubule cells. The tubular damage may be a consequence of or following an existing cardiac dysfunction and/or a cardiovascular disease, including coronary artery disease and heart failure. The present disclosure preferably refers to chronic tubular damage. It is believed that in tubular damage tubule cells become ischemic following heart failure, but it is also believed that tubules have retained their functionality within the kidney entirely or at least to the greatest or a great part. This means that renal function is not impaired or only impaired to a lesser extent, such that CKD or AKI will not be diagnosed. In tubular damage, tubule cells may become dysfunctional, in general by necrosis, and die. However, tubular epithelium regeneration is possible after ischemia and even after necrosis, referred to as "tubular repair" in the context of the present disclosure. According to some embodiments of the present disclosure which refer to chronic tubular injury, some embodiments likewise refer to chronic tubular repair or tubular repair from chronic tubular damage.

In the context of the present disclosure, the term "glomerular damage" refers to epithelial injury in glomerule cells. For example, the glomerular damage may be a consequence of or following an existing cardiac dysfunction and/or a cardiovascular disease, including coronary artery disease and heart failure. The present disclosure also refers to chronic glomerular damage. It is believed that in glomerular damage glomerule cells are ischemic following heart failure, but it is also believed that glomerules have retained their functionality within the kidney entirely or at least to the greatest or a great part. This means that renal function is not impaired or only impaired to a lesser extent, such that CKD or AKI will not be diagnosed. In glomerular damage, glomerule cells may become dysfunctional, in general by necrosis, and die. However, glomerular epithelium regeneration is possible after ischemia and even after necrosis, referred to as "glomerular repair" in the context of the present disclosure. As the present disclosure refers to chronic glomerular injury, it likewise refers to chronic glomerular repair or glomerular repair from chronic glomerular damage.

Renal failure occurs as CKD progresses (chronic renal failure). Renal failure also occurs as a consequence of AKI (acute renal failure). Severe stages of renal failure require dialysis and may be treated by renal transplantation, as the case may be. Acute renal failure may be reversible. AKI may also progress to death.

In this context, the term "renal disorder" is considered to relate, for example, to any disease, injury, or dysfunction of the kidney or affecting the kidney, more particularly affecting the capacity of the kidney for waste removal and/or ultrafiltration. Examples for renal disorders include congenital disorders and acquired disorders.

The term "liver-type fatty acid binding protein" (L-FABP, frequently also referred to as FABP1 herein also referred to as liver fatty acid binding protein) relates to a polypeptide being a liver type fatty acid binding protein and to a variant thereof. Liver-type fatty acid binding protein is an intracellular carrier protein of free fatty acids that is expressed in the proximal tubules of the human kidney. For a sequence of human L-FABP, see e.g. Chan et al.: Human liver fatty acid binding protein cDNA and amino acid sequence, Functional and evolutionary implications, J. Biol. Chem. 260 (5), 2629-2632 (1985) or GenBank Acc. Number M10617.1.

According to embodiments of the instant disclosure, L-FABP is determined in a urine sample of the respective subject, and may also be referred to, in the context of the present disclosure, as "urinary liver-type fatty acid binding protein" or "urinary" L-FABP.

The term "L-FABP" encompasses also variants of L-FABP, such as of human L-FABP. Such variants have at least the same essential biological and immunological properties as L-FABP, i.e. they bind free fatty acids and/or cholesterol and/or retinoids, and/or are involved in intracellular lipid transport. In particular, they share the same essential biological and immunological properties if they are detectable by the same specific assays referred to in this specification, e.g., by ELISA Assays using polyclonal or monoclonal antibodies specifically recognizing the L-FABP. Moreover, it is to be understood that a variant as referred to in accordance with the present disclosure shall have an amino acid sequence which differs due to at least one amino acid substitution, deletion and/or addition wherein the amino acid sequence of the variant is still, in general, at least 50%, 60%, 70%, 80%, 85%, 90%, 92%, 95%, 97%, 98%, or 99% identical with the amino sequence of the human L-FABP. How to determine the degree of identity is specified elsewhere herein. Variants may be allelic variants or any other species specific homologs, paralogs, or orthologs. Moreover, the variants referred to herein include fragments of L-FABP or the aforementioned types of variants as long as these fragments have the essential immunological and biological properties as referred to above. Such fragments may be, e.g., degradation products of the L-FABP. Further included are variants which differ due to posttranslational modifications such as phosphorylation or myristylation. The term "L-FABP" does not include heart FABP, brain FABP and intestine FABP.

Adiponectin is a polypeptide (one of several known adipocytokines) secreted by the adipocyte. In the art, adiponectin is frequently also referred to as Acrp30 and apM1. Adiponectin has recently been shown to have various activities such as anti-inflammatory, antiatherogenic, preventive for metabolic syndrome, and insulin sensitizing activities. Adiponectin is encoded by a single gene, and has 244 amino acids, its molecular weight is approximately 30 kilodaltons. The mature human adiponectin protein encompasses amino acids 19 to 244 of full-length adiponectin. A globular domain is thought to encompass amino acids 107-244 of full-length adiponectin. The sequence of the adiponectin polypeptide is well known in the art, and, e.g., disclosed in WO/2008/084003.

Adiponectin is the most abundant adipokine secreted by adipocytes. Adipocytes are endocrine secretory cells which release free fatty acids and produce, in addition to adiponectin, several cytokines such as tumour necrosis factor (TNF) alpha, leptin, and interleukins.

It is generally assumed that adiponectin sensitizes the body to insulin. Decreased adiponectin blood levels are observed in patients with diabetes and metabolic syndrome and are thought to play a key role in insulin resistance (see e.g. Han et al. Journal of the American College of Cardiology, Vol. 49(5)531-8).

Adiponectin associates itself into larger structures. Three adiponectin polypeptides bind together and form a homotrimer. These trimers bind together to form hexamers or dodecamers. Adiponectin is known to exist in a wide range of multimer complexes in plasma and combines via its collagen domain to create 3 major oligomeric forms: a low-molecular weight (LMW) trimer, a middle-molecular weight (MMW) hexamer, and high-molecular weight (HMW) 12- to 18-mer adiponectin (Kadowaki et al. (2006) Adiponectin and adiponectin receptors in insulin resistance, diabetes, and the metabolic syndrome. J Clin Invest. 116(7): 1784-1792; Rexford S. Ahima, Obesity 2006; 14:242 S-249S). Adiponectin has been reported to have several physiological actions, such as protective activities against atherosclerosis, improvement of insulin sensitivity, and prevention of hepatic fibrosis.

Adiponectin as used herein, preferably, relates to total adiponectin, which encompasses low molecular weight adiponectin, mid molecular weight adiponectin and high molecular weight adiponectin. The terms high molecular weight adiponectin, low and mid molecular weight adiponectin and total adiponectin are understood by the skilled person. According to the instant disclosure, adiponectin may be human adiponectin. Methods for the determination of adiponectin are, e.g., disclosed in US 2007/0042424 A1 as well as in WO/2008/084003. The amount of adiponectin is determined in a urine sample.

The adiponectin referred to in accordance with the present disclosure further encompasses allelic and other variants of said specific sequence for human adiponectin discussed above. For example, embodiments of the instant disclosure include variant polypeptides which are on the amino acid level, at least 50%, 60%, 70%, 80%, 85%, 90%, 92%, 95%, 97%, 98%, or 99% identical, to human adiponectin. The degree of identity between two amino acid sequences can be determined by algorithms well known in the art. The degree of identity may be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT may be employed to determine their optimal alignment and, thus, the degree of identity. For example, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human adiponectin as long as the said polypeptides have adiponectin properties, in particular insulin sensitizing properties.

The term "albumin" refers to a to a globular protein mainly found in blood. They reach a concentration of 3.5 g/dl to 4.5 g/dl and represent approximately 60% of the plasma proteins. Albumin includes human albumin. Mature human albumin comprises 585 amino acids and has a molecular weight of approximately 66,470 Da. The preproprotein has, generally, an amino acid sequence as defined by the NCBI reference sequence NP_000468.1. Albumin plays an important role in maintaining the colloid osmotic pressure of the blood, transports free fatty acids, thyroid hormones, unconjugated bilirubin and many drugs. Moreover, it buffers the pH of the blood.

The term "albumin" encompasses also variants of albumin, for example, of human albumin. Such variants have at least the same essential biological and immunological properties as albumin, i.e. they maintain the colloid osmotic pressure of the blood, and/or transport free fatty acids, and/or transport thyroid hormones, and/or transport unconjugated bilirubin, and/or buffers the pH of the blood. In particular, they share the same essential biological and immunological properties if they are detectable by the same specific assays referred to in this specification, e.g., by ELISA Assays using polyclonal or monoclonal antibodies specifically recognizing the albumin. Moreover, it is to be understood that a variant as referred to in accordance with the present disclosure shall have an amino acid sequence which differs due to at least one amino acid substitution, deletion and/or addition wherein the amino acid sequence of the variant is still, in general, at least 50%, 60%, 70%, 80%, 85%, 90%, 92%, 95%, 97%, 98%, or 99% identical with the amino sequence of the human albumin. How to determine the degree of identity is specified elsewhere herein. Variants may be allelic variants or any other species specific homologs, paralogs, or orthologs. Moreover, the variants referred to herein include fragments of albumin or the aforementioned types of variants as long as these fragments have the essential immunological and biological properties as referred to above. Such fragments may be, e.g., degradation products of the albumin. Further included are variants which differ due to posttranslational modifications such as phosphorylation or myristylation.

The term "neutrophil gelatinase-associated Protein" (NGAL) refers to a protein having a molecular mass of 25 kDa in its glycosylated form and approximately 21 kDa in its deglycosylated form. It comprises 178 amino acids and has an amino acid sequence as described by Kjeldsen et al. in 1993 (Journal of Biological Chemistry, 268: 10425-10432). It is sometimes found as a heterodimer with human neutrophil gelatinase (matrix metalloproteinase 9). Some evidence indicates that binding of NGAL prevents the degradation of matrix metalloproteinase 9 (Yan et al., 2001, Journal of Biological Chemistry, 276: 37258-37265). The expression of NGAL is known to be up-regulated in patients with acute renal dysfunction, especially after renal ischemic injury (Wagener et al., 2006, Anesthesiology, 105: 485-491.

The term "NGAL" encompasses also variants of NGAL, such as, of human NGAL. Such variants have at least the same essential biological and immunological properties as NGAL, i.e. they prevent the degradation of matrix metalloproteinase 9. In particular, they share the same essential biological and immunological properties if they are detectable by the same specific assays referred to in this specification, e.g., by ELISA Assays using polyclonal or monoclonal antibodies specifically recognizing the NGAL. Moreover, it is to be understood that a variant as referred to in accordance with the present disclosure shall have an amino acid sequence which differs due to at least one amino acid substitution, deletion and/or addition wherein the amino acid sequence of the variant is still, in general, at least 50%, 60%, 70%, 80%, 85%, 90%, 92%, 95%, 97%, 98%, or 99% identical with the amino sequence of the human NGAL. How to determine the degree of identity is specified elsewhere herein. Variants may be allelic variants or any other species specific homologs, paralogs, or orthologs. Moreover, the variants referred to herein include fragments of NGAL or the aforementioned types of variants as long as these fragments have the essential immunological and biological properties as referred to above. Such fragments may be, e.g., degradation products of the NGAL. Further included are variants which differ due to posttranslational modifications such as phosphorylation or myristylation.

Determining the amount of adiponectin or a variant thereof, L-FABP or a variant thereof, albumin or a variant thereof, NGAL or a variant thereof or any other peptide or polypeptide referred to in this specification relates to measuring the amount or concentration, either semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present disclosure, determining the amount of a peptide or polypeptide can be achieved by all known means for determining the amount of a peptide in a sample. Said means comprise immunoassay devices and methods which may utilize labelled molecules in various sandwich, competition, or other assay formats. Said assays will develop a signal which is indicative for the presence or absence of the peptide or polypeptide. Moreover, the signal strength can be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, for example, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

According to the instant disclosure, determining the amount of a peptide or polypeptide may comprise the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample may be added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may comprise the steps of (a) contacting the peptide with a specific ligand, (optionally) removing non-bound ligand, (b) measuring the amount of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Exemplary ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present disclosure means that the ligand or agent should not bind substantially to ("cross-react" with) another peptide, polypeptide or substance present in the sample to be analyzed. The specifically bound peptide or polypeptide should be bound with at least 3 times higher, and in some embodiments will be bound with at least 10 times higher and even at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Said method will be semi-quantitative or quantitative. Suitable methods are described in the following.

According to the instant disclosure, the term "antibody" refers to an antibody binding to a peptide selected from the group consisting of L-FABP or a variant thereof, adiponectin or a variant thereof, albumin or a variant thereof and NGAL or a variant thereof.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, the amount of substrate may be saturating. The substrate may also be labeled with a detectable label prior to the reaction. In some embodiments, the sample is contacted with the substrate for an adequate period of time. An adequate period of time refers to the time necessary for a detectable, (and in some cases measurable), amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labelling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag may be at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g. a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

The amount of a peptide or polypeptide may be determined as follows: (a) contacting a solid support comprising a ligand for the peptide or polypeptide as specified above with a sample comprising the peptide or polypeptide and (b) measuring the amount peptide or polypeptide which is bound to the support. The ligand, which may be chosen from the group consisting of nucleic acids, peptides, polypeptides, antibodies and aptamers, may be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

The term "amount" as used herein encompasses the absolute amount of a polypeptide or peptide, the relative amount or concentration of the said polypeptide or peptide as well as any value or parameter which correlates thereto or can be derived there from. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample or a ratio of amounts is compared to a reference ratio of amounts. The comparison referred to in step (c) of the method of the present disclosure may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format.

Based on the comparison of the amount(s) determined in step a) to suitable reference amount(s), it is possible to predict the risk of an individual to suffer from an adverse event related to AKI. It is to be understood that amounts of L-FABP or a variant thereof and, as the case may be, adiponectin or a variant thereof and/or NGAL or a variant thereof and/or albumin or a variant thereof as determined in step (a) of the methods of the presents disclosure are compared in step (b) to reference amounts for of L-FABP or a variant thereof and, as the case may be, adiponectin or a variant thereof and/or NGAL or a variant thereof and/or albumin or a variant thereof as specified elsewhere in this application.

The term "reference amounts" as used herein in this embodiment of the disclosure refers to amounts of the polypeptides which allow diagnosing if an individual does not have an increased risk of suffering from an AKI related adverse event after surgery (in general, this subject is a physiologically healthy subject), or a subject which is not healthy and has an increased risk of suffering from an AKI related adverse event after surgery.

Therefore, the reference amounts will in general be derived from subjects known to be a physiologically healthy, or subjects known to suffer from renal disorder (which may be apparently healthy), or subjects which will be undergoing or having undergone CABG, or subjects known to suffer from renal disorder and which will be undergoing or having undergone CABG.

Accordingly, the term "reference amount" as used herein either refers to an amount which allows to predict the risk of suffering from an adverse event related to AKI in a subject, in particular AKI itself, need for hemodialysis and/or death, and wherein the amounts of the respective marker(s) can be determined prior to the surgical intervention, such as the coronary artery disease related intervention (e.g., a CABG intervention), which the subject is to undergo. The comparison with reference amounts permits to predict or estimate the risk of a subject/individual of suffering from an adverse event related to AKI in a subject, in particular AKI itself, need for hemodialysis and/or death. The individual's need for a surgical intervention may previously have been established prior to determining the markers of the present disclosure.

Reference amounts for L-FABP or a variant thereof and, as the case may be, adiponectin or a variant thereof and/or NGAL or a variant thereof and/or albumin or a variant thereof may be derived from subjects as defined above in the present disclosure which will be undergoing or having undergone a surgical intervention, such as a CABG, and where the subject's outcome was determined, namely occurrence of AKI, need for hemodialysis and/or death. The amounts of the respective peptide serving for establishing the reference amounts can be determined prior to the surgical intervention. In a further embodiment of the present disclosure, the marker(s) are determined at one or various points in time after the surgical intervention, e.g. immediately when terminating intervention, or after 1, 2, 3, 4, 5, 6, 8, 10, 12, 16, 18 or 24 h later.

In embodiments of the present disclosure, the amount/ amounts of the respective markers used therein (L-FABP or a variant thereof and, as the case may be, adiponectin or a variant thereof and/or NGAL or a variant thereof and/or albumin or a variant thereof) may be determined by methods known to the person skilled in the art.

In general, for determining the respective amount(s)/ amount(s) or amount ratios allowing to establish the desired diagnosis in accordance with the respective embodiment of the present disclosure, ("threshold", "reference amount"), the amount(s)/amount(s) or amount ratios of the respective peptide or peptides are determined in appropriate patient groups. According to the diagnosis to be established, the patient group may, for example, comprise only healthy individuals, or may comprise healthy individuals and individuals suffering from the pathophysiological (state which is to be determined, or may comprise only individuals suffering from the pathophysiological state which is to be determined, or may comprise individuals suffering from the various pathophysiological states to be distinguished, by the respective marker(s) using validated analytical methods. The results which are obtained are collected and analyzed by statistical methods known to the person skilled in the art. The obtained threshold values are then established in accordance with the desired probability of suffering from the disease and linked to the particular threshold value. For example, it may be useful to choose the median value, the $60^{th}$, $70^{th}$, $80^{th}$, $90^{th}$, $95^{th}$ or even the $99^{th}$ percentile of the healthy and/or non-healthy patient collective, in order to establish the threshold value(s), reference value(s) or amount ratios.

A reference value of a diagnostic marker can be established, and the amount of the marker in a patient sample can simply be compared to the reference value. The sensitivity and specificity of a diagnostic and/or prognostic test depends on more than just the analytical "quality" of the test-they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker of the disclosure, a distribution of marker amounts for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al, Radiology 143: 29-36 (1982).

In certain embodiments, markers and/or marker panels are selected to exhibit at least about 70% sensitivity, in some cases at least about 80% sensitivity, or even at least about 85% sensitivity, at least about 90% sensitivity, and in some cases at least about 95% sensitivity, combined with at least about 70% specificity, at least about 80% specificity, at least about 85% specificity, at least about 90% specificity, and at least about 95% specificity. In exemplary embodiments, both the sensitivity and specificity are at least about 75% and in some cases at least about 80%, at least about 85%, at least about 90%, and even at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain embodiments, markers and/or marker panels may be selected to exhibit a positive or negative likelihood ratio of at least about 1.5 or more or about 0.67 or less, and in some embodiments at least about 2 or more or about 0.5 or less, and in other embodiments at least about 5 or more or about 0.2 or less, at least about 10 or more or about 0.1 or less, and even at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain exemplary embodiments, markers and/or marker panels may be selected to exhibit an odds ratio of at least about 2 or more or about 0.5 or less, and in some embodiments at least about 3 or more or about 0.33 or less, at least about 4 or more or about 0.25 or less, at least about 5 or more or about 0.2 or less, and even in some embodiments at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain exemplary embodiments, markers and/or marker panels are selected to exhibit a hazard ratio of at least about 1.1 or more or about 0.91 or less, and in some embodiments at least about 1.25 or more or about 0.8 or less, at least about 1.5 or more or about 0.67 or less, at least about 2 or more or about 0.5 or less, and in some embodiments at least about 2.5 or more or about 0.4 or less. The term "about" in this context refers to +/−5% of a given measurement.

While exemplary panels are described herein, one or more markers may be replaced, added, or subtracted from these exemplary panels while still providing clinically useful results. Panels may comprise both specific markers of a disease (e.g., markers that are increased or decreased in bacterial infection, but not in other disease states) and/or non-specific markers (e.g., markers that are increased or decreased due to inflammation, regardless of the cause; markers that are increased or decreased due to changes in hemostasis, regardless of the cause, etc.). While certain markers may not individually be definitive in the methods described herein, a particular "fingerprint" pattern of changes may, in effect, act as a specific indicator of disease state. As discussed above, that pattern of changes may be obtained from a single sample, or may optionally consider temporal changes in one or more members of the panel (or temporal changes in a panel response value).

In order to test if a chosen reference value yields a sufficiently safe diagnosis of patients suffering from the disease of interest, one may for example determine the efficiency (E) of the methods of the disclosure for a given reference value using the following formula:

$$E=(TP/TO)\times 100,$$

wherein TP=true positives and TO=total number of tests=TP+FP+FN+TN, wherein FP=false positives; FN=false negatives and TN=true negatives. E has the following range of values: 0<E<100). According to some embodiments, a tested reference value yields a sufficiently safe diagnosis provided the value of E is at least about 50, at least about 60, at least about 70, at least about 80, at least about 90, at least about 95, and in some cases at least about 98.

The diagnosis if individuals are healthy or suffer from a certain pathophysiological state is made by established methods known to the person skilled in the art. The methods differ in respect to the individual pathophysiological state.

The algorithms to establish the desired diagnosis are laid out in the present application, in the passages referring to the respective embodiment, to which reference is made.

Accordingly, the present disclosure also comprises a method of determining the threshold amount indicative for a physiological and/or a pathological state and/or a certain pathological state, comprising the steps of determining in appropriate patient groups the amounts of the appropriate marker(s), collecting the data and analyzing the data by statistical methods and establishing the threshold values.

The term "about" as used herein refers to +/−20%, preferably +/−10%, preferably, +/−5% of a given measurement or value.

This surprising findings presented herein are of clinical importance as it allows to take an appropriate decision before the intervention and the occurrence of AKI. In this respect, it has to be taken into consideration that after the occurrence of AKI therapeutical option (options for treatment) are clearly more limited than in cases where the risk of suffering from AKI is recognized and its occurrence can be treated prophylactically. Such decisions include reconsideration of the indication for surgery in terms of improving risk benefit assessment, discontinuation of drugs known to precipitate AKI including ACE inhibitors, angiotensin receptor blockers and NSIADs and potentially antibiotics and other drugs known to precipitate AKI. Furthermore during surgery appropriate and intense balancing of fluid as well as blood pressure is required. Thus the method of the present disclosures targets prophylaxis of AKI thus provides improved clinical decision making.

Accordingly, the methods of the present disclosure lend themselves in particular for adults. In exemplary embodiments, the method of risk prediction, the method of recommending or deciding on a suitable therapy and the method of monitoring the therapy are applied to adults; in further embodiments, these cited methods are not applied to children.

Surprisingly it was found that the amount of L-FABP or a variant thereof is a good predictor for future events related to AKI when determined before intervention is carried out. It was also found that the amount of adiponectin when determined before intervention may add complementary information to that provided by L-FABP or a variant thereof. Further information may be added by determining the amount of albumin or a variant thereof and/or NGAL or a variant thereof before intervention.

Major surgery interventions, in particular major cardiovascular surgery interventions, are associated with significant mortality and morbidity, including the development of acute kidney injury (AKI). AKI may resolve without dialysis or, if prolonged, may require dialysis, or may even be associated with future chronic renal disorder. Currently, risk of development of AKI or even need for dialysis cannot be predicted in patients with normal kidney function (as assessed by creatinine levels within the normal range of the test or a GFR above 60 ml/min). However, thanks to the present disclosure, L-FABP can be used to identify patients at risk even before surgery. Only a risk assessment before surgery, for example in the course of a risk/benefit analysis, allows to reconsider indication for surgery, discontinuation of drugs precipitating AKI (although they may be indicated because of the underlying disease(s)) and to take appropriate measure during surgery (maintenance of blood pressure, avoidance of temporary hypovolemia, and further measures known to the person skilled in the art).

L-FABP is a urinary biomarker which is expressed in the proximal tubule epithelial cells in the postischemic kidney. As adiponectin appears to be an indicator of "glomerular health", combined determination of these markers disclose relevant information of pathogenic kidney processes.

In further embodiments of the present disclosure, albumin and/or NGAL are determined further to L-FABP and adiponectin. NGAL is a marker of tubular damage, albumin is a marker of glomerular damage, permitting gathering supplementary information.

Advantageously, as described herein it has been found that the amount of L-FABP or a variant thereof as a biomarker, in particular the amount of L-FABP or a variant thereof present in sample, for example a urine-sample of a subject, can predict the risk of an individual of suffering from an adverse event related to acute kidney injury AKI following a surgical intervention in a reliable and efficient manner, as reflected by the high specificity and sensitivity of the method of the present disclosure as evidenced in the examples.

It has also been found that the amount of adiponectin or a variant thereof as a biomarker, in particular the amount of adiponectin or a variant thereof present in a urine-sample of a subject predict the risk of an individual of suffering from an adverse event related to acute kidney injury AKI following a surgical intervention in a reliable and efficient manner. L-FABP or a variant thereof and adiponectin or a variant thereof give complementary information in respect to the risk of an individual to suffer from an adverse event related to acute kidney injury.

AKI may progress to a need for dialysis and even to death (which both are considered, in the context of the present disclosure, to be adverse events related to acute kidney injury). In an exemplary embodiment of the present disclosure, the amounts of L-FABP or a variant thereof and/or adiponectin or a variant thereof, for example a combination of the two, may be used to predict the risk of an individual to develop a need for dialysis as a consequence of or following a surgical intervention.

A "need for dialysis" occurs in individuals suffering from renal failure, in the context of the present disclosure acute renal failure (AKI), wherein the extent or degree of renal failure (as determined by GFR and/or creatinine clearance) impairs renal function such that the urine production and removal of electrolytes and wastes (which are removed by filtration in healthy kidneys body's) does not comply with body's needs and may seriously affect the individual's health, in particular cause non-reversible health impairment. An example is anemia which is frequently observed as a consequence of diminished erythropoietin synthesis.

The term "surgical intervention" in the context of the present disclosure refers to any kind of invasive intervention on the body of an animal, for example a mammal such as a human, by a surgical method (including major surgery). The surgical intervention may be indicated because of a vascular disease, a trauma, a bleeding disorder, a tumor, e.g. a benign or malignant tumor, an infection or for other reasons. Surgery may be of short or prolonged duration may be associated with pre-existing fluid or blood loss or during the surgical procedure itself. The surgical procedure may be carried out with or without localized or general anaesthesia. The term may also include minimal invasive surgery, even though the complications which are cited in the present application for occurring after surgery are less frequently observed after minimal invasive surgery.

The term "major surgery" as used in the context of the present disclosure refers to any surgery that requires anesthesia and/or respiratory assistance.

The term "surgical intervention" also includes e.g. interventions on the extremities (legs, arms), and the head. The term includes interventions on inner organs, (e.g. liver, kidney, bowel, stomach, lung, without being exhaustive). The term also includes interventions of on the heart (e.g. on the valve or any part of the myocard), also termed cardiovascular surgery.

Patients undergoing cardiovascular surgery frequently suffer from heart failure as a consequence of or following a cardiovascular disease and, most importantly, pre-existing kidney disease.

According to the instant disclosure, the term also refers to interventions on the heart vessels (also termed cardiovascular surgery), for example bypass grafting.

In coronary artery bypass grafting (CABG) native coronary arteries with high-grade stenosis or occlusion not appropriate for performing angioplasty with stenting are bypassed typically using an artery as a pedicled graft to the left anterior descending coronary artery. The term and its meaning are known to the person skilled in the art.

It is known to the person skilled in the art that, in principle, any surgical intervention may cause AKI related adverse events. It is believed that this phenomenon may be due to the existence of non-recognized renal disorders in the respective individuals (meaning that the individuals are apparently healthy) which induce a higher probability to suffer from an AKI related adverse event. In some embodiments, the non-recognized renal disorder is present before the surgical intervention. Frequently, the renal disorders are a consequence of ischemic and/or necrotic processes, in general after an impaired blood supply leading to non-compliance with the kidneys' metabolic needs. Ischemic and necrotic processes, in turn, frequently are caused by cardiovascular diseases, preferably coronary artery disease (CAD).

In consequence, there is an increased probability that an individual not showing obvious signs and symptoms of a renal disorder, as indicated by GFR and/or creatinine values, and which is apparently healthy in the sense of the present disclosure, will develop an AKI related adverse event undergoing cardiovascular surgery, in particular in the context of CAD and/or heart failure.

The term "cardiovascular disease" as used in the context of the present disclosure is known to the person skilled in the art and relates to any dysfunction observed in the coronary vessels and the heart itself, and includes, in particular, coronary artery disease CAD.

The term "cardiovascular surgery" refers to surgery carried out in the context of cardiovascular diseases. In some embodiments the term relates to surgery carried out in the context of CAD, which may also be referred to as "CAD surgery".

"Coronary artery disease" (CAD) as used in the context of the present disclosure is known to the person skilled in the art and involves impairment of blood flow through the coronary arteries, in many cases by arteriosclerotic processes, in general atheromas, which may cause ischemia, angina pectoris, acute coronary syndromes (unstable angina pectoris, myocardial infarction MI) and sudden cardiac death. Treatment includes drugs and procedures to reduce ischemia and restore or improve coronary blood flow. Usually, CAD is due to deposition of atheromas in large and medium-sized coronary arteries (atherosclerosis). Less often, CAD is due to coronary spasm. Rare causes include coronary artery embolism, dissection, aneurysm, and vasculitis. In the context of the present disclosure, CAD also includes heart failure.

According to the method of the disclosure increased amounts of L-FABP or a variant thereof in comparison to reference amounts measured in a sample, for example a urinary sample of a subject are indicative for a tubular damage of the kidney. Increased amounts of NGAL or a variant thereof in comparison to reference amounts measured in a sample of a subject are indicative for a tubular damage of the kidney. Increased amounts of adiponectin or a variant thereof in comparison to reference amounts are indicative for a glomerular damage of the kidney. Increased amounts of albumin or a variant thereof in comparison to reference amounts are indicative for a glomerular damage of the kidney. Increased amounts of L-FABP or a variant thereof and/or increased amounts of NGAL or a variant thereof, in combination with increased amounts of adiponectin or a variant thereof and/or increased amounts of albumin or a variant thereof, in comparison to reference amounts, are indicative for a progressive tubular and glomerular damage of the kidney.

In the context of the present disclosure, one embodiment refers to the case that the marker amounts are determined prior to carrying out the surgical intervention for example, such as at least or up to about 4 weeks, at least or up to about 2 weeks prior to the intervention, or at least or up to about 7 days, or at least or up to about 3 days, or at least or up to about 1 day, or at least or up to about 20 h, or at least or up to about 12 h, or at least or up to about 6 h prior to the surgical intervention. In the case of acute events occurring after the determination of the amounts of the markers, the amounts may be determined again.

In exemplary embodiments of the present disclosure, the following reference amounts for the markers are used, where the marker amount is determined in a sample taken prior to the surgical intervention. The amounts of each marker are normalized in respect to creatinine ("creatinine for . . . "), in order to eliminate inaccuracies resulting from variations in urine volume of the respective individual.

Acute kidney injury and need for dialysis in AKI are known complications of major surgery and specifically after cardiac surgery and to occur within 72 hours (or 3 days) after surgery. Calculation of the average risk of these complications is known to the person skilled in the art. (McIlroy D. R. et al, Clin J. Am Soc Nephrol 5: 211-219, 2010). Average risk depends among others on the underlying disease, comorbidities and type of intervention which form the basis for calculation of the average risk. The terms "high risk", "higher risk", "very high risk" as used in the context of the present disclosure relate to those cases where the risk is increased relative to average risk. The terms "low risk", "lower risk", "very low risk" as used in the context of the present disclosure relate to those cases where the risk is decreased relative to average risk.

L-FABP:

According to embodiments of the present disclosure, a reference amount of ≤about 3.6 µg/g; ≤about 3.2 µg/g; and ≤about 2.9 µg/g, creatinine for L-FABP or a variant thereof, is indicative that the individual is at a low risk; at lower risk; at a very low risk of suffering from AKI (rule out).

According to embodiments of the present disclosure, a reference amount of ≥about 10.8 µg/g; ≤about 29.5 µg/g; ≥about 32.3 µg/g, creatinine for L-FABP or a variant thereof, is indicative that the individual is at a high risk; at higher risk; at a very high risk of suffering from AKI (rule in).

According to embodiments of the present disclosure, a reference amount of ≤about 4.2 µg/g; ≤about 3.2 µg/g; ≤about 2.8 µg/g, creatinine for L-FABP or a variant thereof, is indicative that the individual is at a low risk; at lower risk; at a very low risk of suffering from need for dialysis (rule out).

According to embodiments of the present disclosure, a reference amount of ≥about 35.4 µg/g; ≤about 36.2 µg/g; ≥about 37.2 µg/g, creatinine for L-FABP or a variant thereof, is indicative that the individual is at a high risk; at higher risk; at a very high risk of suffering from need for dialysis (rule in).

Adiponectin:

In case additionally the amount of adiponectin or a variant thereof is determined, the reference values indicating a risk suffering from AKI/need for dialysis is at low risk and at high risk of suffering from AKI/need for dialysis is the following:

According to embodiments of the present disclosure, a reference amount of ≤about 3.6 µg/g; ≤about 3.2 µg/g; ≤about 2.8 µg/g, creatinine for adiponectin or a variant thereof, is indicative that the individual is at a low risk; at lower risk; at a very low risk of suffering from AKI (rule out).

According to embodiments of the present disclosure, a reference amount of ≥about 15.6 µg/g; ≤about 17.6 µg/g; ≥about 30.0 µg/g, creatinine for adiponectin or a variant thereof, is indicative that the individual is at a high risk; at higher risk; at a very high risk of suffering from AKI (rule in).

According to embodiments of the present disclosure, a reference amount of ≤about 8.8 µg/g; ≤about 3.2 µg/g; ≤about 1.2 µg/g, creatinine for adiponectin or a variant thereof, is indicative that the individual is at a low risk; at lower risk; at a very low risk of suffering from need for dialysis (rule out).

According to embodiments of the present disclosure, a reference amount of ≥about 30.4 µg/g; ≤about 135.2 µg/g; ≥about 171.6 µg/g, creatinine for adiponectin or a variant thereof, is indicative that the individual is at a high risk; at higher risk; at a very high risk of suffering from need for dialysis (rule in).

Adiponectin gives information independently from L-FABP.

Albumin:

In case additionally the amount of albumin or a variant thereof is determined, the reference values indicating a risk suffering from AKI/need for dialysis is at low risk and at high risk of suffering from AKI/need for dialysis is the following:

According to embodiments of the present disclosure, a reference amount of ≤about 6 µg/g; ≤about 4 µg/g; ≤about 2 µg/g, creatinine for albumin or a variant thereof, is indicative that the individual is at a low risk; at lower risk; at a very low risk of suffering from AKI (rule out).

According to embodiments of the present disclosure, a reference amount of ≥about 128 µg/g; ≤about 142 µg/g; ≥about 160 µg/g, creatinine for albumin or a variant thereof, is indicative that the individual is at a high risk; at higher risk; at a very high risk of suffering from AKI (rule in).

According to embodiments of the present disclosure, a reference amount of ≤about 8 µg/g; ≤about 4 µg/g; ≤about 2 µg/g, creatinine for albumin or a variant thereof, is indicative that the individual is at a low risk; at lower risk; at a very low risk of suffering from need for dialysis (rule out).

According to embodiments of the present disclosure, a reference amount of ≥about 54 µg/g; ≤about 128 µg/g; ≥about 142 µg/g, creatinine for albumin or a variant thereof, is indicative that the individual is at a high risk; at higher risk; at a very high risk of suffering from need for dialysis (rule in).

Albumin gives information independently from L-FABP.

NGAL:

In case additionally the amount of NGAL or a variant thereof is determined, the reference values indicating a risk suffering from AKI/need for dialysis is at low risk and at high risk of suffering from AKI/need for dialysis is the following:

According to embodiments of the present disclosure, a reference amount of ≤about 7.0 µg/g; ≤about 5.5 µg/g; ≤about 3.5 µg/g, creatinine for NGAL or a variant thereof, is indicative that the individual is at a low risk; at lower risk; at a very low risk of suffering from AKI (rule out).

According to embodiments of the present disclosure, a reference amount of ≥about 12 µg/g; ≤about 13 µg/g; ≥about 14 µg/g, creatinine for NGAL or a variant thereof, is indicative that the individual is at a high risk; at higher risk; at a very high risk of suffering from AKI (rule in).

According to embodiments of the present disclosure, a reference amount of ≤about 9.0 µg/g; ≤about 7.5 µg/g; ≤about 1.5 µg/g, creatinine for NGAL or a variant thereof, is indicative that the individual is at a low risk; at lower risk; at a very low risk of suffering from need for dialysis (rule out).

According to embodiments of the present disclosure, a reference amount of ≥about 15.0 µg/g; ≤about 20.5 µg/g; ≥about 26.5 µg/g, creatinine for NGAL or a variant thereof, is indicative that the individual is at a high risk; at higher risk; at a very high risk of suffering from need for dialysis (rule in).

NGAL gives information independently from L-FABP.

In one embodiment of the present disclosure, one or more of the marker L-FABP or a variant thereof, adiponectin or a variant thereof, albumin or a variant thereof and NGAL or a variant thereof are determined at surgery termination or following surgery termination. By this, the risk for suffering from AKI and/or need for dialysis can be determined. The one or more markers are determined at the end of surgery (i.e. within a few minutes up to about 1 hour after surgery termination) and/or may be determined in intervals thereafter, e.g. about 2 h, 4 h, 5 h, 6 h, 10 h, 12 h, 16 h, 24 h after termination of surgery.

The amounts of albumin or a variant thereof determined at or after surgery termination permit to differentiate between individuals at risk of future occurrence of acute kidney injury and those not at risk, when determined immediately after surgery. Also, the amounts of albumin or a variant thereof permit to differentiate between individuals at risk of future need for dialysis and those not at risk, when determined after surgery. Even though albumin or a variant thereof amounts decrease rapidly after termination of surgery, determining albumin or a variant thereof amounts within about 6 to 24 h, and according to some embodiments of the instant disclosure about 6 to 12 h after surgery termination are still able to discriminate between patients at risk and not at risk, both for AKI and dialysis.

When determined after surgery, for example at about 6 h after surgery termination, a reference amount of ≤about 8 µg/g, and ins some embodiments herein ≤about 5 µg/g, or ≤about 4 µg/g, creatinine for albumin or a variant thereof, is indicative that the individual is at a low risk, lower risk, and even at a very low risk of suffering from AKI (rule out).

When determined after surgery, for example at about 12 h after surgery termination, a reference amount of ≤about 8 µg/g, and ins some embodiments herein ≤about 4 µg/g, or ≤about 2 µg/g, creatinine for albumin or a variant thereof, is indicative that the individual is at a low risk, lower risk, and even at a very low risk of suffering from AKI (rule out).

When determined after surgery, for example at about 6 h after surgery termination, a reference amount of ≤about 8 µg/g, and ins some embodiments herein ≤about 6 µg/g, or ≤about 4 µg/g, creatinine for albumin or a variant thereof, is indicative that the individual is at a low risk, lower risk, and even at a very low risk of suffering from need for dialysis (rule out).

When determined after surgery, for example at about 12 h after surgery termination, a reference amount of ≤about 10 µg/g, and in some embodiments herein ≤about 4 µg/g, or ≤about 2 µg/g, creatinine for albumin or a variant thereof, is indicative that the individual is at a low risk, lower risk, and even at a very low risk of suffering from need for dialysis (rule out).

The amounts of adiponectin or a variant thereof determined at or after surgery termination permit to differentiate between individuals at risk of future need for dialysis and those not at risk, when determined after surgery. Even though adiponectin or a variant thereof amounts increase rapidly after termination of surgery, determining adiponectin amounts within about 6 to 24 h, and in some embodiments of the instant disclosure about 6 to 12 h after surgery termination are still able to discriminate between patients at risk and not at risk for dialysis.

When determined after surgery, for example at about 6 h after surgery termination, a reference amount of ≤about 65 µg/g, and in some embodiments herein ≤about 48 µg/g, or ≤about 24 µg/g creatinine for adiponectin or a variant thereof, is indicative that the individual is at a low risk, lower risk, and even at a very low risk, and even at an even lower risk of suffering from need for dialysis (rule out).

When determined after surgery, for example at about 12 h after surgery termination, a reference amount of ≤about 72 µg/g, and in some embodiments herein ≤about 62 µg/g, or ≤about 47 µg/g creatinine for adiponectin or a variant thereof, is indicative that the individual is at a low risk, at lower risk, and even at a very low risk, and even at an even lower risk of suffering from need for dialysis (rule out).

The amounts of L FABP or a variant thereof determined at or after surgery termination were lower in patients developing AKI than in those who did not, presumably because of preexisting kidney disease. Determining adiponectin or a variant thereof amounts not immediately after surgery termination, but after about 6 to 24 h, and in some embodiments herein about 6 to 12 h after surgery termination, is able to discriminate between patients at risk and not at risk for need of dialysis.

When determined after surgery, for example at about 6 h after surgery termination, a reference amount of ≤about 10 µg/g, and in some embodiments herein ≤about 5 µg/g, or ≤about 0 µg/g, creatinine for L-FABP or a variant thereof, is indicative that the individual is at a low risk, at lower risk, and even at a very low risk of suffering from need for dialysis (rule out).

When determined after surgery, for example at about 12 h after surgery termination, a reference amount of ≤about 10 µg/g, and in some embodiments herein ≤about 5 µg/g, or ≤about 2 µg/g, creatinine for L-FABP or a variant thereof, is indicative that the individual is at a low risk, at lower risk, and even at a very low risk of suffering from need for dialysis (rule out).

The amounts of NGAL or a variant thereof determined at or after surgery termination permit to differentiate between individuals at risk of future need for dialysis and those not at risk. Determining NGAL amounts or those of a variant thereof about 6 to 24 h, and in some embodiments herein about 6 to 12 h after surgery termination is able to discriminate between patients at risk and not at risk for need of dialysis.

When determined after surgery, for example at about 6 h after surgery termination, a reference amount of ≤about 20 µg/g, and in some embodiments herein ≤about 15 µg/g, or ≤about 10 µg/g, creatinine for NGAL or a variant thereof, is indicative that the individual is at a low risk, at lower risk, and even at a very low risk of suffering from need for dialysis (rule out).

When determined after surgery, for example at about 12 h after surgery termination, a reference amount of ≤about 30 µg/g, and in some embodiments herein ≤about 20 µg/g, or ≤about 10 µg/g, creatinine for NGAL or a variant thereof, is indicative that the individual is at a low risk, at lower risk, and even at a very low risk of suffering from need for dialysis (rule out).

The present disclosure also relates to a method of recommending or deciding on a suitable therapy in a subject being at risk of experiencing an adverse event related to acute kidney injury AKI after a surgical intervention in a subject, based on predicting the risk of the adverse event related to AKI by the comparison of the amounts of liver-type fatty acid binding protein (L-FABP) or a variant thereof, determined in a sample of said subject, to at least one reference amount.

This method of the present disclosure comprises at least one of the following steps and/or may comprise the following steps: a) determining the amounts of liver-type fatty acid binding protein (L-FABP) or a variant thereof, for example urinary liver-type fatty acid binding protein (L-FABP) or a variant thereof, in a sample, such as a urine-sample of a subject; b) comparing the amounts determined in step a) with reference amounts; c) predicting the risk based on the comparison carried out in step b); d) recommending or deciding the initiation of a suitable therapy or refraining from the suitable therapy, based on the information obtained in step c).

The present disclosure also provides a method of recommending or deciding on a suitable therapy in a subject being at risk of experiencing an adverse event related to acute kidney injury AKI after a surgical intervention in a subject, comprising the steps of: a) determining liver-type fatty acid binding protein (L-FABP) or a variant thereof, such as urinary liver-type fatty acid binding protein (L-FABP) or a variant thereof, in sample, such as a urine-sample of a subject; b) comparing the amounts determined in step a) with reference amounts; and c) predicting the risk based on the comparison carried out in step b) and d) recommending or deciding the initiation of a suitable therapy or refraining from the suitable therapy, based on the information obtained in step c).

In another embodiment of the present disclosure, the present disclosure provides a method of recommending or deciding on a suitable therapy in a subject being at risk of experiencing an adverse event related to acute kidney injury AKI after a surgical intervention in a subject, comprising the steps of: a) determining the amounts of liver-type fatty acid binding protein (L-FABP) or a variant thereof, such as urinary liver-type fatty acid binding protein (L-FABP) or a variant thereof, in a sample, for example a urine-sample of a subject; and b) comparing the amounts determined in step a) with reference amounts; whereby the risk of the subject to experience adverse event related to acute kidney injury AKI after a surgical intervention is predicted and the initiation of or the refraining from a suitable therapy is recommended based on the prediction.

In an exemplary embodiment of the present disclosure, the amount of adiponectin or a variant thereof is determined in the urine sample further to the amount of L-FABP or a variant thereof, and the recommendation is established based on the comparison of the marker amounts with reference amounts.

In further embodiments of the present disclosure, the amount of at least one further marker selected from albumin or a variant thereof and neutrophil gelatinase associated lipocalin (NGAL) or a variant thereof is measured in the urine sample, and the recommendation is established based on the comparison of the marker amounts with reference amounts. In this embodiment, the amount of only one additional marker from the above-cited group further to L-FABP or a variant thereof and, for example adiponectin or a variant thereof will be measured, or the amounts of both additional markers further to L-FABP or a variant thereof and, for example, adiponectin or a variant thereof.

In the method of recommending or deciding on a suitable therapy as disclosed beforehand, the respective markers may be determined prior to surgery. In a further embodiment of the present disclosure, the marker(s) are determined after surgical intervention has been terminated, e.g. immediately when terminating intervention, or after 1, 2, 3, 4, 5, 6, 8, 10, 12, 16, 18 or 24 h later.

In further embodiments of the present disclosure, suitable therapies are the administration of pharmaceuticals and/or life style recommendations which are effective in respect of inhibition of further progression of kidney disease.

Advantageously, the method of the present disclosure allows the identification of patients with an increased risk of AKI prior to the surgical intervention and/or following the surgical intervention. From the determination of an increased risk of AKI in a patient, known risk factors that precipitate AKI can be controlled in a patient having an increased risk of suffering from AKI after a surgical procedure. Control of these risk factors includes careful fluid balance during and after surgery. If a cardiopulmonary bypass is used during surgery, low perfusion temperatures have to be avoided. Nephrotoxic drugs (e.g. non-steroidal anti-inflammatory drugs and sulfonamides) have to be avoided as well. Moreover, the administration of erythropoietin may be indicated (Song et al., 2009, American Journal of Nephrology, 253-260). The possibility to predict the risk of acute kidney injury after a surgical intervention in a patient prior to said intervention and/or after said intervention obviously has consequences for deciding whether the patient in question is eligible for the surgical procedure in question.

The term "susceptible" as used herein means that a therapy applied to a subject will inhibit or ameliorate the progression of diabetes mellitus or its accompanying symptoms. It is to be understood assessment for susceptibility for the therapy will not be correct for all (100%) of the investigated subjects. However, it is envisaged that at least a statistically significant portion can be determined for which the therapy can be successfully applied. Whether a portion is statistically significant can be determined by techniques specified elsewhere herein.

Furthermore, the present disclosure relates to a method of monitoring the therapy in a subject being at risk of an adverse event related to acute kidney injury AKI as a consequence of a surgical intervention in a subject, based on predicting the risk of an adverse event related to AKI by the comparison of the amounts of liver-type fatty acid binding protein (L-FABP), such as urinary L-FABP or a variant thereof, determined in a sample of said subject at various points in time (at least two different points in time), to at least one reference amount.

This method of the present disclosure comprises at least one of the following steps and/or may comprise the following steps: a) determining the amounts of liver-type fatty acid binding protein (L-FABP) or a variant thereof, in a sample, such as a urine-sample of a subject at various points in time (at least two different points in time); b) comparing the amounts determined in step a) with reference amounts; c) predicting the risk based on the comparison carried out in step b); d) monitoring the therapy, based on the information obtained in step c).

The present disclosure also provides a method of monitoring the therapy in a subject being at risk of an adverse event related to acute kidney injury AKI as a consequence of a surgical intervention in a subject, comprising the steps of: a) determining the amounts of liver-type fatty acid binding protein (L-FABP) or a variant thereof, in a urine-sample of a subject at various points in time (at least two different points in time); b) comparing the amounts determined in step a) with reference amounts; and c) predicting the risk based on the comparison carried out in step b) and d) recommending or deciding the initiation of a suitable therapy or refraining from the suitable therapy, based on the information obtained in step c).

In another embodiment of the present disclosure, the present disclosure provides a method of monitoring the therapy in a subject being at risk of an adverse event related to acute kidney injury AKI as a consequence of a surgical intervention in a subject, comprising the steps of: a) determining the amounts of liver-type fatty acid binding protein (L-FABP) or a variant thereof, in a urine-sample of a subject at various points in time (at least two different points in time); b) comparing the amounts determined in step a) with reference amounts; whereby the risk of the subject to experience adverse event related to acute kidney injury AKI after a surgical intervention is predicted and the initiation of or refraining from a suitable therapy is recommended based on the prediction.

In an exemplary embodiment of the present disclosure, the amount of adiponectin or a variant thereof is determined in the urine sample further to the amount of L-FABP or a variant thereof, and monitoring is carried out based on the comparison of the marker amounts with reference amounts.

In additional exemplary embodiments of the present disclosure, the amount of at least one further marker selected from albumin or a variant thereof and neutrophil gelatinase associated lipocalin (NGAL) or a variant thereof is measured in the urine sample, and monitoring is carried out based on the comparison of the marker amounts with reference amounts. In such embodiments, the amount of only one additional marker from the above-cited group further to L-FABP or a variant thereof and, for example, adiponectin or a variant thereof will be measured, or the amounts of both additional markers further to L-FABP or a variant thereof and, for example, adiponectin or a variant thereof.

"Monitoring" as used herein relates to keeping track of the pathophysiological state of the respective individual relative to AKI related events, such as AKI itself or need for dialysis, occurrence and/or progression of the disease or the influence of a particular treatment on the progression of disease. Monitoring means control after about 1 day, about 2 day, about 3 days, about 5 days, about 7 day, about 10 days, about 12 days, about 14 days.

In one embodiment, the present disclosure provides a method for diagnosing acute kidney injury AKI in a subject, comprising the steps of: a) determining the amounts of liver-type fatty acid binding protein (L-FABP) or a variant thereof, such as a urine-sample of a subject; b) comparing the amounts determined in step a) with reference amounts; and c) diagnosing AKI based on the steps carried out in step b).

The present disclosure also provides a method for diagnosing acute kidney injury AKI in a subject, comprising the steps of: a) determining the amounts of liver-type fatty acid binding protein (L-FABP) or a variant thereof, such as a urine-sample of a subject; and b) comparing the amounts determined in step a) with reference amounts; wherein AKI is diagnosed based on the steps carried out in step b).

Moreover, the present disclosure also includes kits and devices adapted to carry out the method of the present disclosure. Furthermore, the present disclosure relates to a device for predicting the risk of an adverse event related to acute kidney injury AKI as a consequence of a surgical intervention in a subject, comprising: a) means for determining the amounts of liver-type fatty acid binding protein, such as urinary liver-type fatty acid binding protein (L-FABP) or a variant thereof, and, as the case may be, adiponectin or a variant thereof and/or NGAL or a variant thereof and/or albumin or a variant thereof, in a sample, for example a urine-sample of a subject; b) means for comparing the amounts determined in step a) with reference amounts; and c) predicting the risk based on the comparison carried out in step b), and whereby the device is adapted for diagnosing the kidney damage.

Moreover the present disclosure is concerned with a kit for predicting the risk of an adverse event related to acute kidney injury AKI as a consequence of a surgical intervention in a subject, comprising: a) means for determining the amounts of liver-type fatty acid binding protein, for example a urinary liver-type fatty acid binding protein (L-FABP) or a variant thereof, and, as the case may be, adiponectin or a variant thereof and/or NGAL or a variant thereof and/or albumin or a variant thereof, in a sample, for example a urine-sample of a subject; b) means for comparing the amounts determined in step a) with reference amounts; and c) predicting the risk based on the comparison carried out in step b), and whereby the kit is adapted for diagnosing the kidney damage.

The term "device" as used herein relates to a system of means comprising at least the aforementioned means operatively linked to each other as to allow predicting the risk of an adverse event related to acute kidney injury AKI as a consequence of a surgical intervention in a subject, and/or recommending or deciding on a suitable therapy in a subject being at risk of an adverse event related to acute kidney injury AKI as a consequence of a surgical intervention in a subject, and/or monitoring the therapy in a subject being at risk of an adverse event related to acute kidney injury AKI as a consequence of a surgical intervention in a subject, based on predicting the risk of an adverse event related to AKI in a subject. Exemplary means for determining the amount of (L-FABP), and, as the case may be, adiponectin or a variant thereof and/or NGAL or a variant thereof and/or albumin or a variant thereof, and means for carrying out the comparison are disclosed above in connection with the method of the disclosure. How to link the means in an operating manner will depend on the type of means included into the device. For example, where means for automatically determining the amount of the peptides are applied, the data obtained by said automatically operating means can be processed by, e.g., a computer program in order to obtain the desired results. According to the instant disclosure, the means may be comprised by a single device in such a case. Said device may accordingly include an analyzing unit for the measurement of the amount of the peptides or polypeptides in an applied sample and a computer unit for processing the resulting data for the evaluation. Alternatively, where means such as test stripes are used for determining the amount of the peptides or polypeptides, the means for comparison may comprise control stripes or tables allocating the determined amount to a reference amount. The test strips may be coupled to a ligand which specifically binds to the peptides or polypeptides referred to herein. According to the instant disclosure, the strip or device may comprise means for detection of the binding of said peptides or polypeptides to the said ligand. Exemplary means for detection are disclosed in connection with embodiments relating to the method of the disclosure above. In such a case, the means are operatively linked in that the user of the system brings together the result of the determination of the amount and the diagnostic or prognostic value thereof due to the instructions and interpretations given in a manual. The means may appear as separate devices in such an embodiment and may be packaged together as a kit. The person skilled in the art will realize how to link the means. Exemplary devices are those which can be applied without the particular knowledge of a specialized clinician, e.g., test strips or electronic devices which merely require loading with a sample. The results may be given as output of raw data which need interpretation by the clinician. In some embodiments, the output of the device is, however, processed, i.e. evaluated, raw data the interpretation of which does not require a clinician. Further exemplary devices comprise the analyzing units/devices (e.g., biosensors, arrays, solid supports coupled to ligands specifically recognizing L-FABP or a variant thereof, and, as the case may be, adiponectin or a variant thereof and/or NGAL or a variant thereof and/or albumin or a variant thereof, Plasmon surface resonance devices, NMR spectrometers, mass-spectrometers etc.) or evaluation units/devices referred to above in accordance with the method of the disclosure.

The term "kit" as used herein refers to a collection of the aforementioned means, provided separately or within a single container. Optionally, the kit may additionally comprise a user's manual for interpreting the results of any measurement(s) with respect to predicting the risk of an adverse event related to acute kidney injury AKI as a consequence of a surgical intervention in a subject, and/or recommending or deciding on a suitable therapy in a subject being at risk of an adverse event related to acute kidney injury AKI as a consequence of a surgical intervention in a subject, and/or monitoring the therapy in a subject being at risk of an adverse event related to acute kidney injury AKI as a consequence of a surgical intervention in a subject, based on predicting the risk of an adverse event related to AKI, as defined in the present disclosure. Particularly, such manual may include information about what determined amounts corresponds to what kind of diagnosis. This is outlined in detail elsewhere in this specification. Additionally, such user's manual may provide instructions about correctly using the components of the kit for determining the amount of the respective biomarkers.

The present disclosure also relates to the use of a kit or device for determining the amount of L-FABP or a variant thereof, and, as the case may be, adiponectin or a variant thereof and/or NGAL or a variant thereof and/or albumin or a variant thereof, in a sample of a subject, and/or the use of means for determining the amount of L-FABP or a variant thereof, and, as the case may be, adiponectin or a variant thereof and/or NGAL or a variant thereof and/or albumin or a variant thereof, and/or the use of means for comparing the amount of L-FABP or a variant thereof, and, as the case may be, adiponectin or a variant thereof and/or NGAL or a variant thereof and/or albumin or a variant thereof, to at least one reference amount, for: predicting the risk of an adverse event related to acute kidney injury AKI as a consequence of a surgical intervention in a subject, and/or recommending or deciding on a suitable therapy in a subject being at risk of an adverse event related to acute kidney injury AKI as a consequence of a surgical intervention in a subject, and/or monitoring the therapy in a subject being at risk of an adverse event related to acute kidney injury AKI as a consequence of a surgical intervention in a subject, wherein all uses are based on predicting the risk of an adverse event related to AKI in a subject.

According to embodiments of the instant disclosure, the prediction of the risk of an adverse event related to acute kidney injury AKI as a consequence of a surgical intervention is based on a sample taken prior to the surgical intervention. The present disclosure also relates to the use of: an antibody to L-FABP or a variant thereof, and, as the case may be, an antibody to adiponectin or a variant thereof and/or an antibody to NGAL or a variant thereof and/or an antibody to albumin or a variant thereof, and/or of means for determining the amount of L-FABP or a variant thereof, and, as the case may be, means for determining the amount adiponectin or a variant thereof and/or means for determining the amount of NGAL or a variant thereof and/or of means for determining the amount of albumin or a variant thereof, and/or of means for comparing the amount of L-FABP or a variant thereof, and, as the case may be, adiponectin or a variant thereof and/or NGAL or a variant thereof and/or albumin or a variant thereof, to at least one reference amount for the manufacture of a diagnostic composition for: predicting the risk of an adverse event related to acute kidney injury AKI as a consequence of a surgical intervention in a subject, and/or recommending or deciding on a suitable therapy in a subject being at risk of an adverse event related to acute kidney injury AKI as a consequence of a surgical intervention in a subject, and/or monitoring the therapy in a subject being at risk of an adverse event related to acute kidney injury AKI as a consequence of a surgical intervention in a subject, wherein all uses are based on predicting the risk of an adverse event related to AKI in a subject.

According to some embodiments of the instant disclosure, the prediction of the risk of an adverse event related to acute kidney injury AKI as a consequence of a surgical intervention is based on a sample taken prior to the surgical intervention.

The present disclosure also relates to the use of: an antibody to L-FABP or a variant thereof, and, as the case may be, an antibody to adiponectin or a variant thereof and/or an antibody to NGAL or a variant thereof and/or an antibody to albumin or a variant thereof, and/or of means for determining the amount of L-FABP or a variant thereof, and, as the case may be, of means for determining the amount adiponectin or a variant thereof, and/or of means for determining the amount of NGAL or a variant thereof and/or of means for determining the amount of albumin or a variant thereof, and/or of means for comparing the amount of L-FABP or a variant thereof, and, as the case may be, adiponectin or a variant thereof and/or NGAL or a variant thereof and/or albumin or a variant thereof, to at least one reference amount for: predicting the risk of an adverse event related to acute kidney injury AKI as a consequence of a surgical intervention in a subject, and/or recommending or deciding on a suitable therapy in a subject being at risk of an adverse event related to acute kidney injury AKI as a consequence of a surgical intervention in a subject, and/or monitoring the therapy in a subject being at risk of an adverse event related to acute kidney injury AKI as a consequence of a surgical intervention in a subject, wherein all uses are based on predicting the risk of an adverse event related to AKI in a subject.

According to embodiments of the instant disclosure, the prediction of the risk of an adverse event related to acute kidney injury AKI as a consequence of a surgical intervention is based on a sample taken prior to the surgical intervention.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for predicting the risk of a subject to experience an adverse event related to acute kidney injury (AKI) after a surgical intervention, comprising the steps of:
    a) determining the amounts of liver-type fatty acid binding protein (L-FABP) or a variant thereof, in a sample, preferably a urine-sample, of a subject obtained before the surgical intervention; and
    b) comparing the amounts determined in step a) with reference amounts; and
    whereby the risk of the subject to experience adverse event related to acute kidney injury AKI after a surgical intervention is predicted.
2. The method according to 1, wherein additionally the amount of adiponectin or a variant thereof is determined in the sample and the risk is predicted based on the comparison of the marker amounts with respective reference amounts
3. The method according to 1 or 2, wherein the amount of at least one further marker selected from albumin or a variant thereof and neutrophil gelatinase associated lipocalin (NGAL) or a variant thereof is measured in the sample, and the risk is predicted based on the comparison of the marker amounts with respective reference amounts.
4. The method according to any of 1 to 3, wherein a reference amount of ≤about 3.6 µg/g creatinine for L-FABP or a variant thereof is indicative that the individual is at a low risk of suffering from AKI, and a reference amount of ≥about 10.8 µg/g, creatinine for L-FABP or a variant thereof, is indicative that the individual is at a high risk of suffering from AKI, when determined prior to carrying out the surgical intervention.
5. The method according to any of 1 to 4, wherein a reference amount of ≤about 4.2 µg/g creatinine for L-FABP or a variant thereof, is indicative that the individual is at a low risk of suffering from need for dialysis, and a reference amount of ≥about 35.4 µg/g creatinine for L-FABP or a variant thereof is indicative that the individual is at a high risk of suffering from need for dialysis, when determined prior to carrying out the surgical intervention.

6. The method according to any of 1 to 5, wherein a reference amount of ≤about 3.6 µg/g creatinine for adiponectin or a variant thereof is indicative that the individual is at a low risk of suffering from AKI, and a reference amount of ≥about 15.6 µg/g creatinine for adiponectin or a variant thereof is indicative that the individual is at a high risk of suffering from AKI, when determined prior to carrying out the surgical intervention.
7. The method according to any of 1 to 6, wherein a reference amount of ≤about 8.8 µg/g creatinine for adiponectin or a variant thereof is indicative that the individual is at a low risk of suffering from need for dialysis, and a reference amount of ≥about 30.4 µg/g creatinine for adiponectin or a variant thereof is indicative that the individual is at a high risk of suffering from need for dialysis, when determined prior to carrying out the surgical intervention.
8. A method for diagnosing acute kidney injury AKI in a subject, comprising the steps of:
    a) determining the amounts of liver-type fatty acid binding protein (L-FABP) or a variant thereof, preferably a urine-sample of a subject; and
    b) comparing the amounts determined in step a) with reference amounts;
    wherein AKI is diagnosed based on the comparison of step b).
9. A method of recommending a suitable therapy in a subject being at risk of experiencing an adverse event related to acute kidney injury AKI after a surgical intervention, comprising the steps of:
    a) determining the amounts of liver-type fatty acid binding protein (L-FABP) or a variant thereof, in a urine-sample of a subject;
    b) comparing the amounts determined in step a) with reference amounts; and
    whereby the risk of the subject to experience adverse event related to acute kidney injury AKI after a surgical intervention is predicted and the initiation of or refraining from a suitable therapy is recommended based on the prediction.
10. A method of monitoring the therapy in a subject being at risk of an adverse event related to acute kidney injury AKI as a consequence of a surgical intervention in a subject, comprising the steps of:
    a) determining the amounts of liver-type fatty acid binding protein (L-FABP) or a variant thereof, in a sample, preferably a urine-sample of a subject at various points in time (at least two different points in time); and
    b) comparing the amounts determined in step a) with reference amounts; and
    whereby the risk of the subject to experience adverse event related to acute kidney injury AKI after a surgical intervention is predicted and the initiation of or refraining from a suitable therapy is recommended based on the prediction.
11. Use of an anti-L-FABP antibody for predicting the risk of a subject to experience an adverse event related to acute kidney injury (AKI) after a surgical intervention.
12. Use of an anti-L-FABP antibody for recommending or deciding on a suitable therapy in a subject being at risk of experiencing an adverse event related to acute kidney injury AKI after a surgical intervention.
13. A device for predicting the risk of an adverse event related to acute kidney injury AKI as a consequence of a surgical intervention in a subject, comprising:
    a) means for determining the amounts of liver-type fatty acid binding protein (L-FABP) or a variant thereof, and, as the case may be, adiponectin or a variant thereof and/or NGAL or a variant thereof and/or albumin or a variant thereof, in a sample, preferably a urine-sample of a subject;
    b) means for comparing the amounts determined in step a) with reference amounts; and
    c) means for predicting the risk based on the comparison carried out in step b), and
    whereby the device is adapted for diagnosing the kidney damage.
14. A kit for predicting the risk of an adverse event related to acute kidney injury AKI as a consequence of a surgical intervention in a subject, comprising:
    a) means for determining the amounts of liver-type fatty acid binding protein (L-FABP) or a variant thereof, and, as the case may be, adiponectin or a variant thereof and/or NGAL or a variant thereof and/or albumin or a variant thereof, in a sample, preferably a urine-sample of a subject;
    b) means for comparing the amounts determined in step a) with reference amounts; and
    c) means for predicting the risk based on the comparison carried out in step b), and
    whereby the device is adapted for diagnosing the kidney damage.

EXAMPLES

In the following examples, the following tests were used for the determination of the amounts of the respective peptides:

L-FABP was determined by using the L-FABP ELISA-Kit from CMIC Co., Ltd, Japan The test was based on an ELISA 2-step assay. L-FABP standard or urine samples were firstly treated with pretreatment solution as provided with the test, and transferred into a L-FABP antibody coated microplate containing assay buffer and incubated. During this incubation, L-FABP in the reaction solution bound to the immobilized antibody. After washing, the $2^{nd}$ Antibody-POD conjugate was added as the secondary antibody and incubated, thereby forming sandwich of the L-FABP antigen between the immobilized antibody and conjugate antibody. After incubation, the plate was washed and substrate for enzyme reaction was added, color develops according to the L-FABP antigen quantity. The L-FABP concentration was determined based on the optical density. The assay had a measuring range from 3 ng/ml to 400 ng/ml.

Adiponectin (multimeric) was determined by using the test EIA from ALPCO DIAGNOSTICS® (USA), operating on the principle of a "sandwich" format ELISA. The specific antibodies used in the kit were anti-human adiponectin monoclonal antibodies (MoAbs) directed to two independent epitopes. The specimens were pre-treated as described below, and total adiponectin and individual multimers of adiponectin were determined selectively, directly or indirectly. Multimers of adiponectin were classified into four fractions with this kit:
   1) Total adiponectin fraction: "Total-Ad"-assayed directly on the plate
   2) High-molecular adiponectin fraction (equivalent of dodecamer-octodecamer): "HMW-Ad"-assayed directly on the plate
   3) Middle-molecular adiponectin fraction (equivalent of hexamer): "MMW-Ad"-inferred value obtained by subtracting the concentration of HMW-Ad from the combined concentration of MMW-Ad+HMW-Ad 4) Low-molecular adiponectin fraction (equivalent of trimer including albumin-binding adiponectin): "LMWAd"-inferred value obtained by subtracting the combined concentration of MMW-Ad+HMW-Ad from the total concentration of Ad. The microtiter plate wells had been coated with an anti-human adiponectin monoclonal antibody. Adiponectin in the standards and pretreated specimens was captured by the antibody during the first incubation. Afterwards, a wash step removed all unbound material. Subsequently, an anti-human adiponectin antibody which had been biotin-labeled was added and bound to the immobilized adiponectin in the wells. Subsequently, an anti-human adiponectin antibody which had been biotin-labeled was added and bound to the immobilized adiponectin in the wells. After the second incubation and subsequent wash step, HRP-labeled streptavidin was added. After the third incubation and subsequent wash step, substrate solution was added. Finally, stop reagent was added after allowing the color to develop. The intensity of the color development was read by a microplate reader. The absorbance value reported by the plate reader was proportional to the concentration of adiponectin in the sample. The test kit was effective in the range from 0.075 ng/ml to 4.8 ng/ml.

NGAL was determined by the NGAL Rapid ELISA Kit from BIOPORTO® Diagnostics, Denmark. The assay was an ELISA performed in microwells coated with a monoclonal antibody against human NGAL. Bound NGAL was detected with a horseradish peroxidase (HRP)-conjugated monoclonal antibody and the assay was developed by incubation with a color-forming substrate. The assay used a rapid 2-step procedure:

Step 1.

Aliquots of calibrators, diluted samples and any controls were incubated with HRP-conjugated detection antibody in the coated microwells. Only NGAL would bind to both coat and detection antibody, while unbound materials were removed by washing.

Step 2.

A chromogenic peroxidase substrate containing tetramethylbenzidine (TMB) was added to each test well. The HRP linked to the bound detection antibody reacted with the substrate to generate a colored product. The enzymatic reaction was stopped chemically, and the color intensity was read at 450 nm in an ELISA reader. The color intensity (absorbance) was a function of the concentration of NGAL originally added to each well. The results for the calibrators were used to construct a calibration curve from which the concentrations of NGAL in the test specimens were read.

Albumin was determined by using the COBAS® Tinaquant Albumin test (Roche Diagnostics) by immuno-turbidometry. The test principle was the recognition of albumin by a specific anti-albumin antibody forming a complex with albumin, which was determined after agglutination. The assay had a measuring range in urine between 3 ng/ml and 400 ng/ml.

The named tests were also preferably employed in the general context of the present disclosure for the determination of the respective peptides.

In order to optimize reference values that would predict the likelihood of complications to occur or not to occur receiver operating curves (ROC curves) were constructed. Complications in the context of the current disclosure are acute kidney injury as defined or need for dialysis. Timepoints for determination of the likelihood of complications to occur or not to occur were preferably pre surgery. This timepoint allows to take all appropriate measures to avoid such complications including the possibility not to perform the surgery as has been outlined in the present disclosure. Post surgery or even later measures to avoid or ameliorate such complications are much more limited, however with regard to the risk to dialysis such information will provide appropriate time to prepare for such a complication, e.g. availability for dialysis equipment, transport to appropriate unit, more intensive surveillance etc.

Example 1

A total of 126 patients (median age 63 years), creatinine within normal range, undergoing elective coronary bypass surgery were evaluated for the presence of kidney injury markers before, after and 6, 12 and 24 hours after intervention.

89 patients did not develop AKI, AKI was recognized in 37 patients as indicated by an increase in creatinine by at least 0.3 mg/dl, 12 patients developed need for dialysis and 9 died within 30 days after surgery.

The following urinary kidney markers were measured: Albumin, adiponectin, L-FABP and NGAL. The results are presented in the ROC curves 1-18 (see above).

Figure 2:
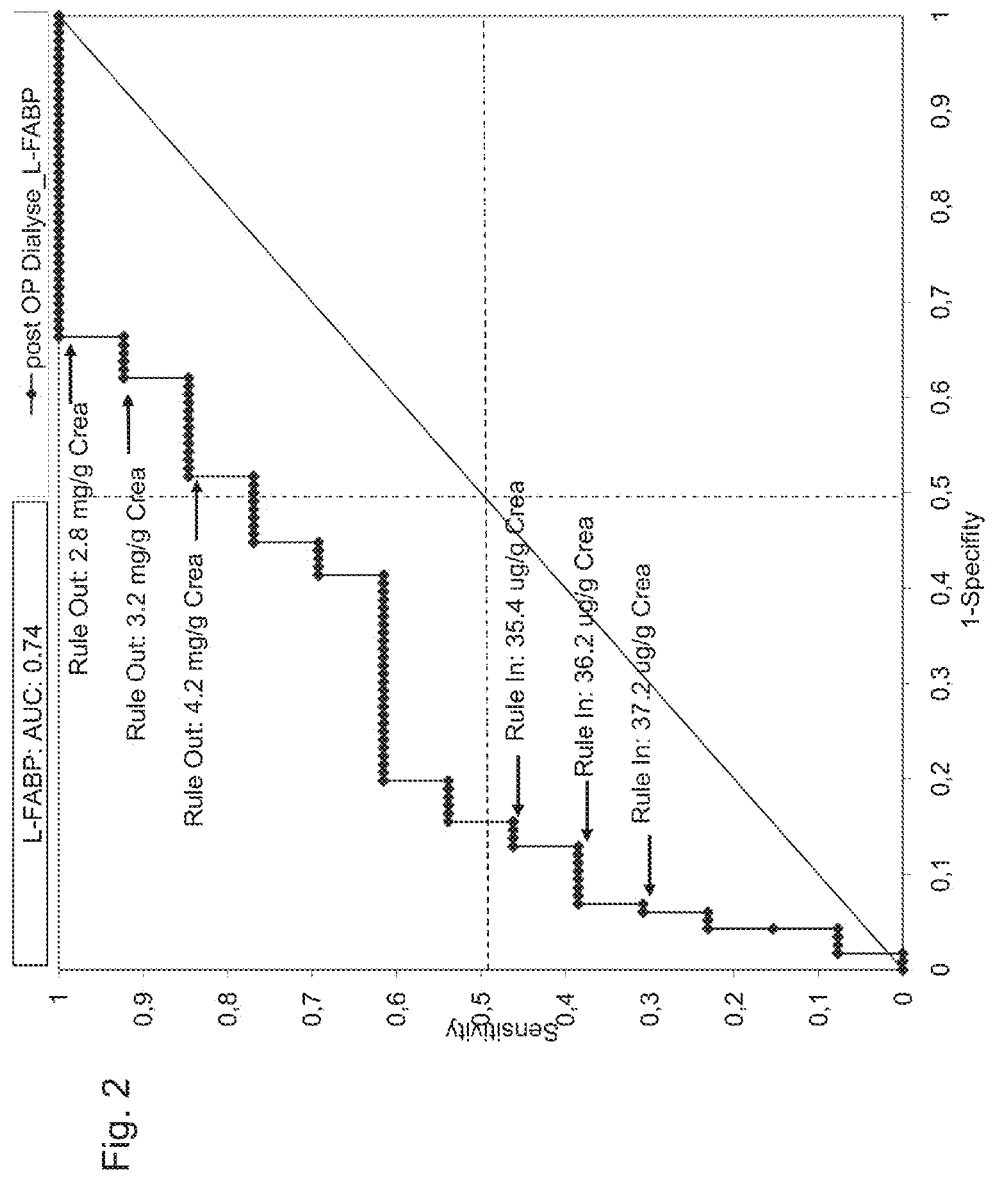
FIG. 2 is a ROC analysis for urinary L FABP of samples obtained from the patients described in Example 1 before surgery in which analysis was performed with respect to the need for dialysis (yes or no).
Figure 3:
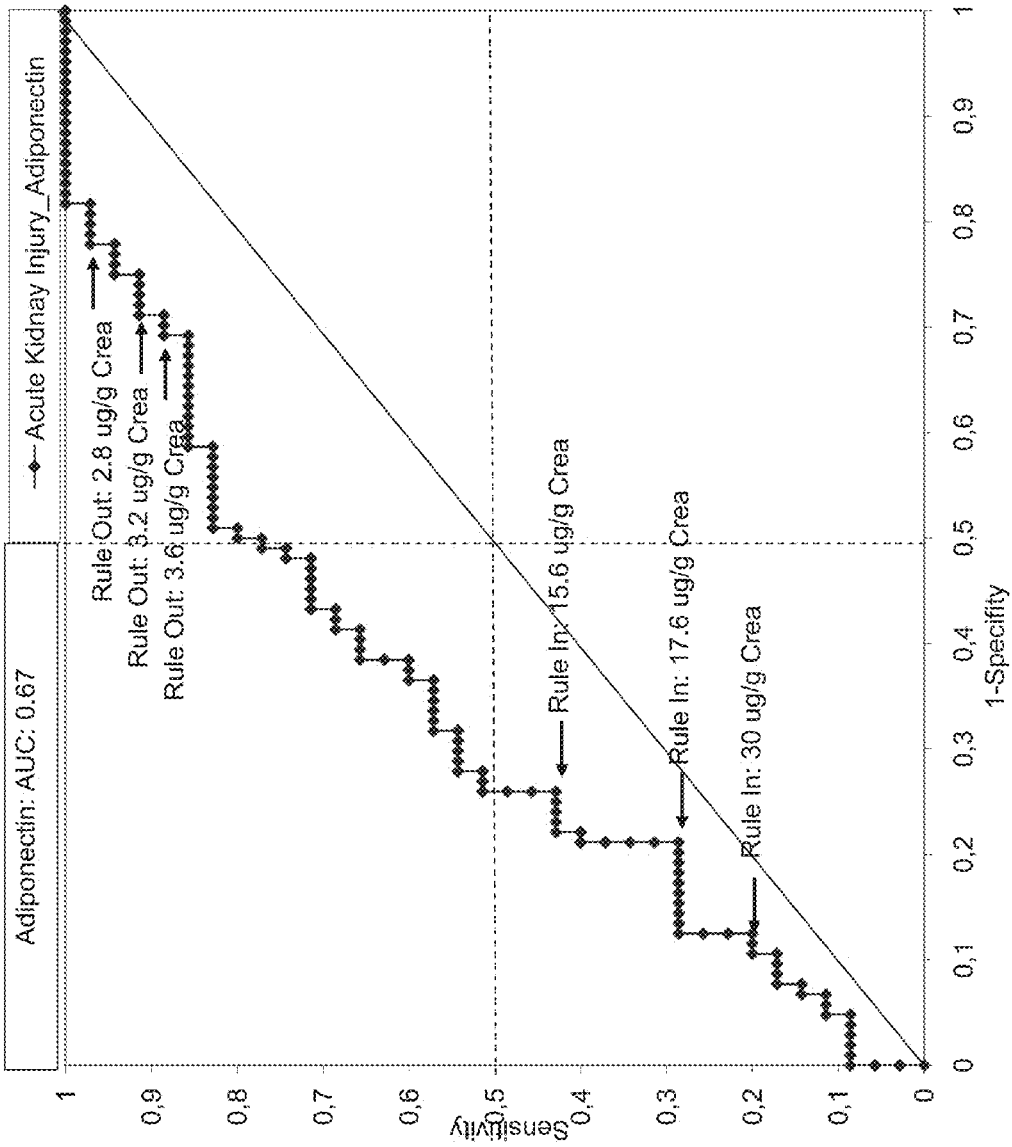
FIG. 3 is a ROC analysis for adiponectin of samples obtained from the patients described in Example 1 before surgery in which analysis was performed with respect to the clinical endpoint acute kidney injury (yes or no).
Figure 4:
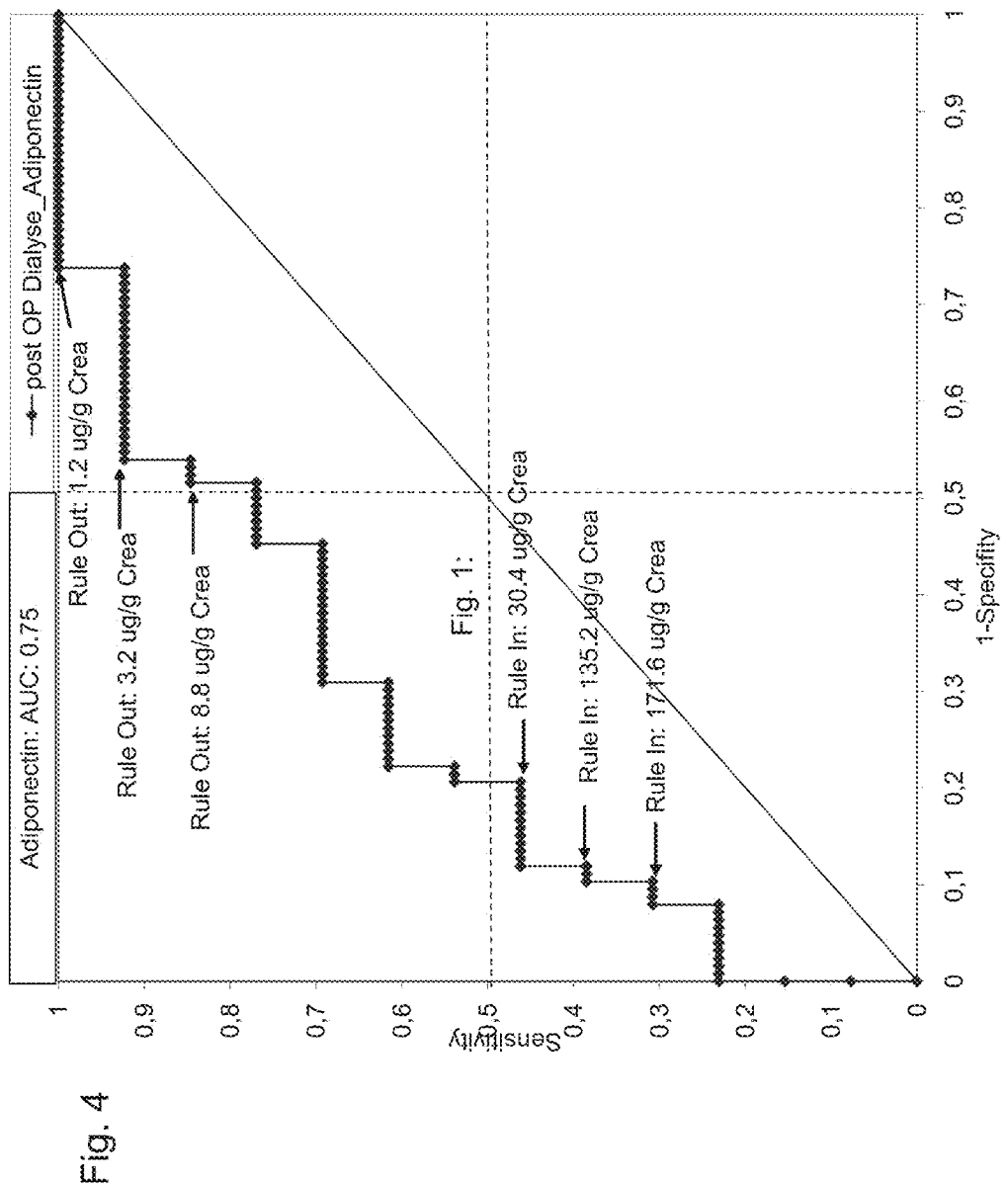
FIG. 4 is a ROC analysis for adiponectin of samples obtained from the patients described in Example 1 before surgery in which analysis was performed with respect to the need for dialysis (yes or no).
Figure 5:
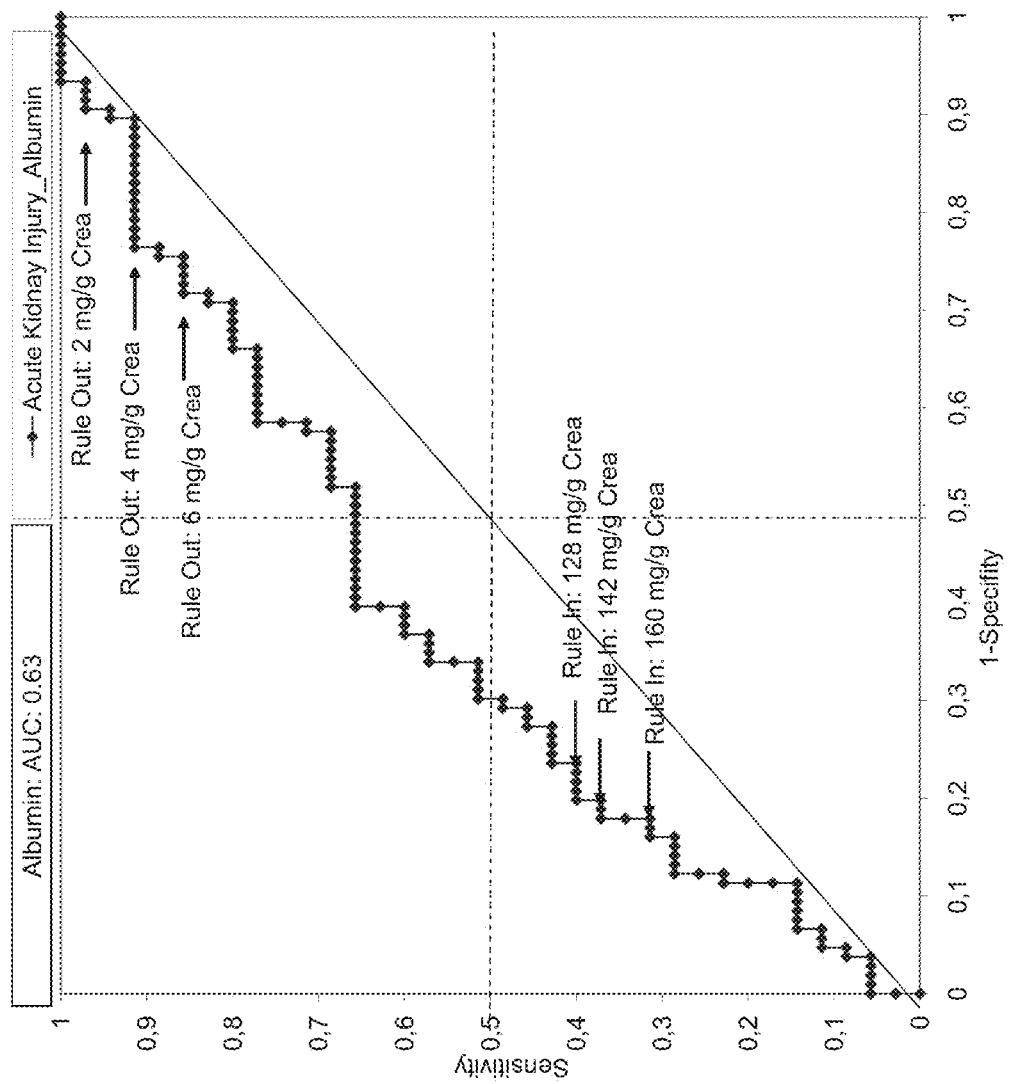
FIG. 5 is a ROC analysis for albumin of samples obtained from the patients described in Example 1 before surgery in which analysis was performed with respect to the clinical endpoint acute kidney injury (yes or no).
Figure 6:
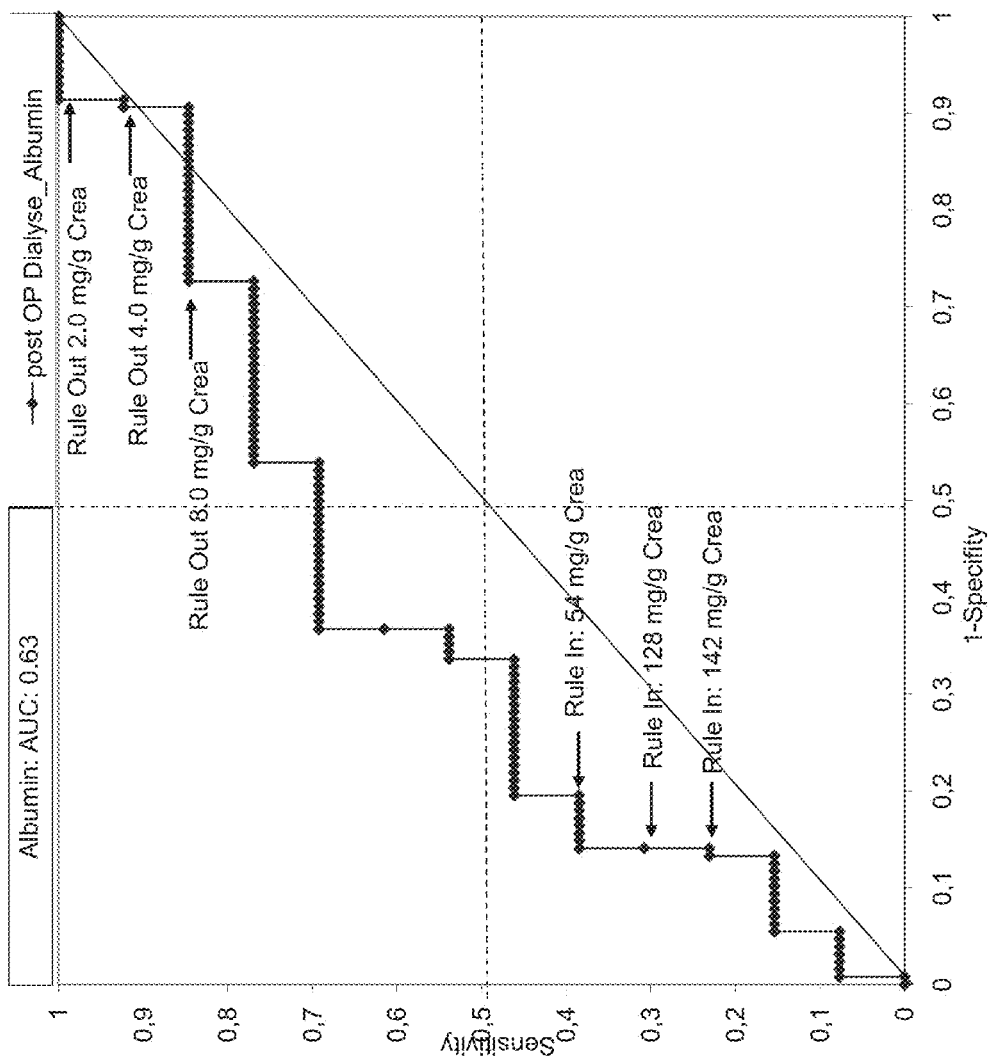
FIG. 6 is a ROC analysis for albumin of samples obtained from the patients described in Example 1 before surgery in which analysis was performed with respect to the need for dialysis (yes or no).
Figure 7:
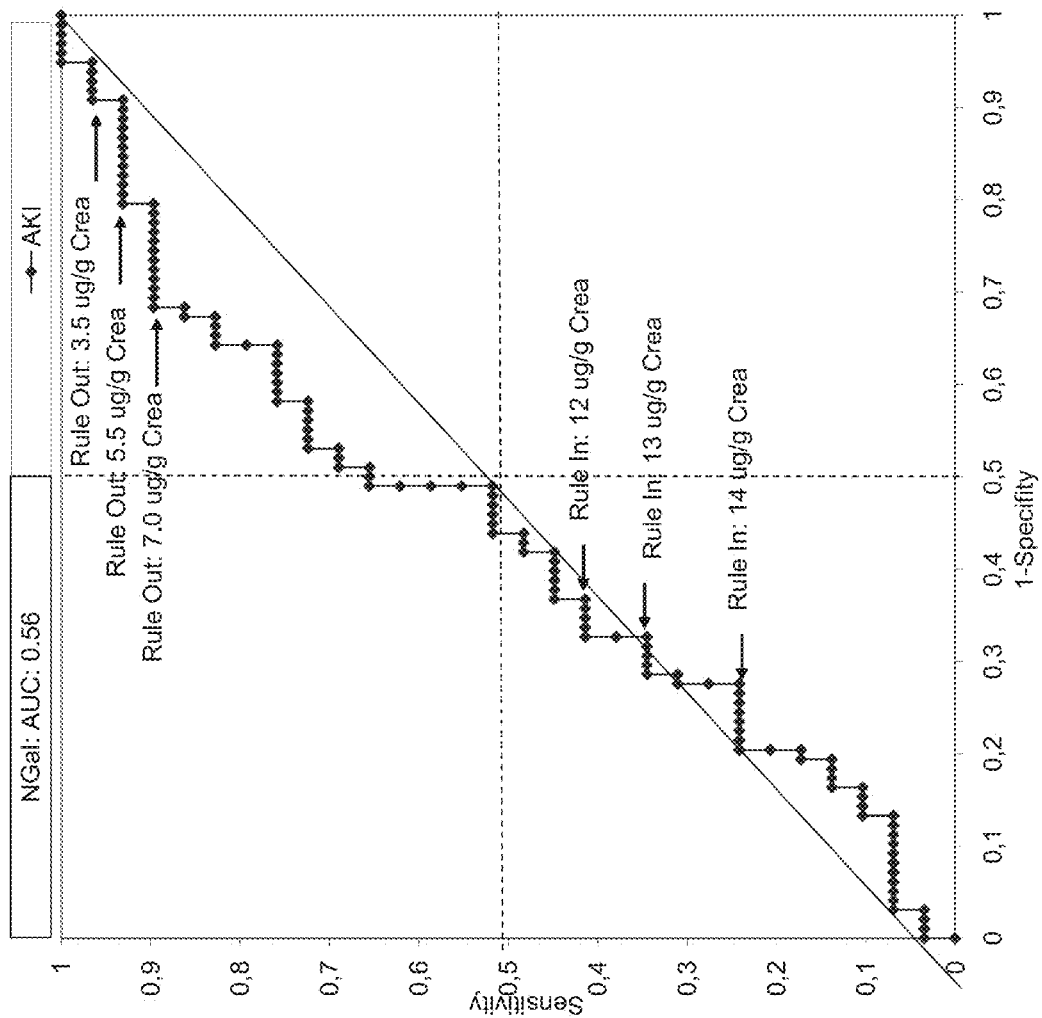
FIG. 7 is a ROC analysis for NGAL of samples obtained from the patients described in Example 1 before surgery I which analysis was performed with respect to the clinical endpoint acute kidney injury (yes or no).
Figure 8:
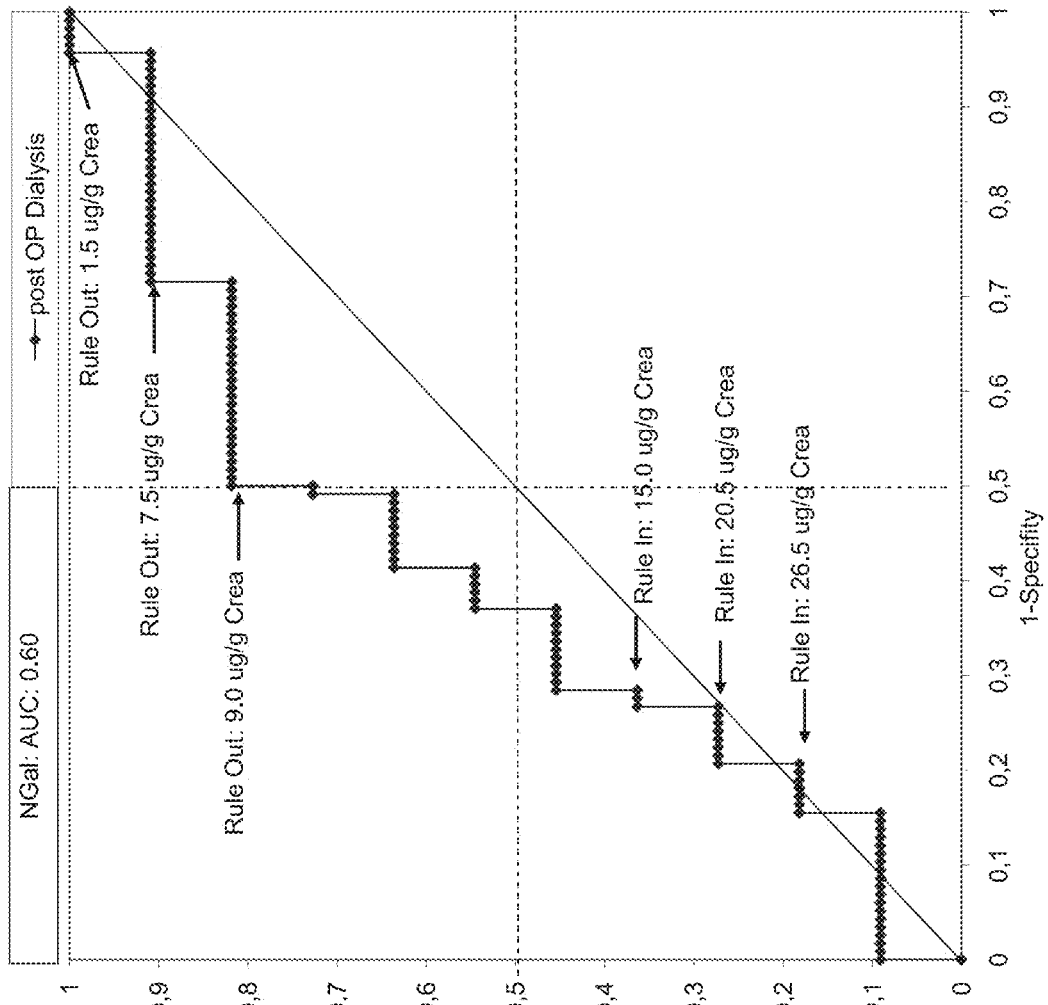
FIG. 8 is a ROC analysis for NGAL of samples obtained from the patients described in Example 1 before surgery in which analysis was performed with respect to the need for dialysis (yes or no).
Figure 9:
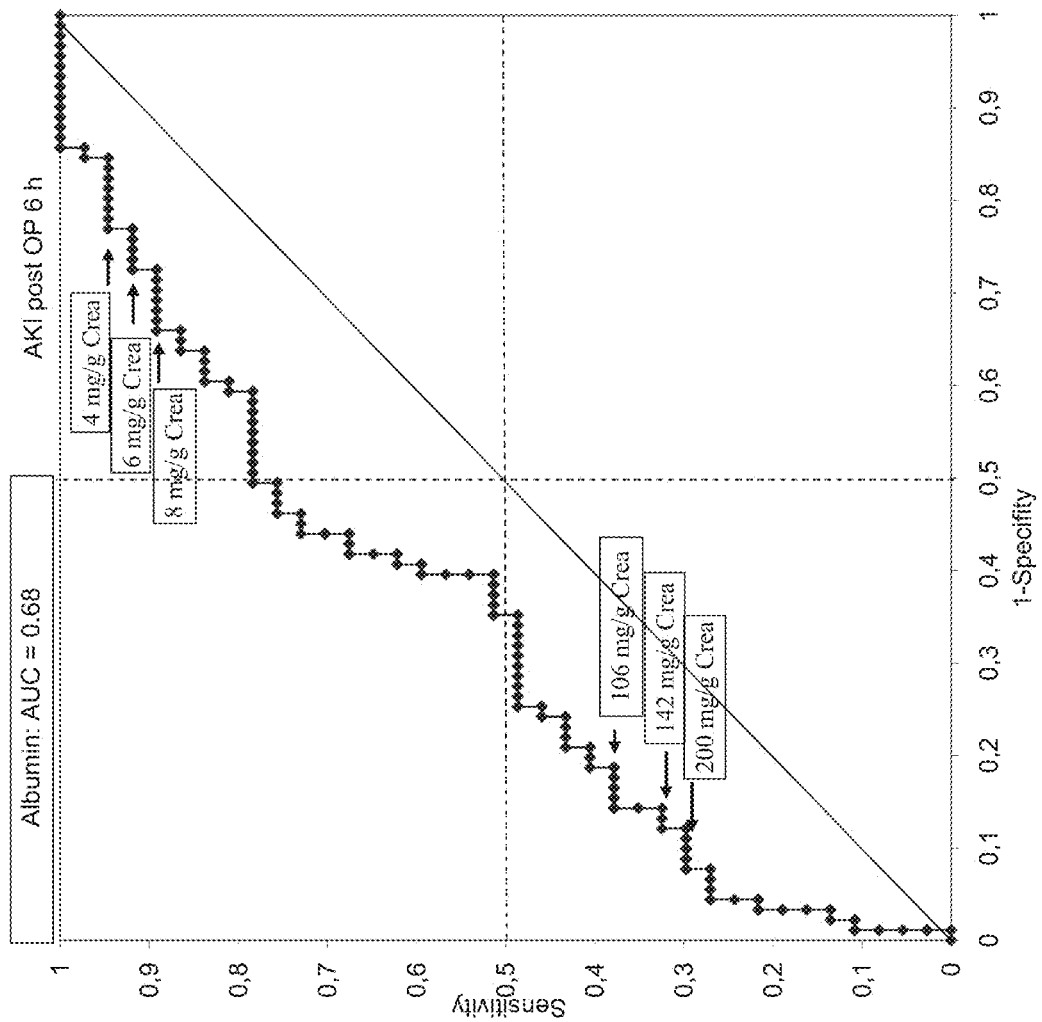
FIG. 9 is a ROC analysis for albumin of samples obtained from the patients described in Example 1 about 6 h after surgery termination, in which analysis was performed with respect to the clinical endpoint acute kidney injury (yes or no).
Figure 10:
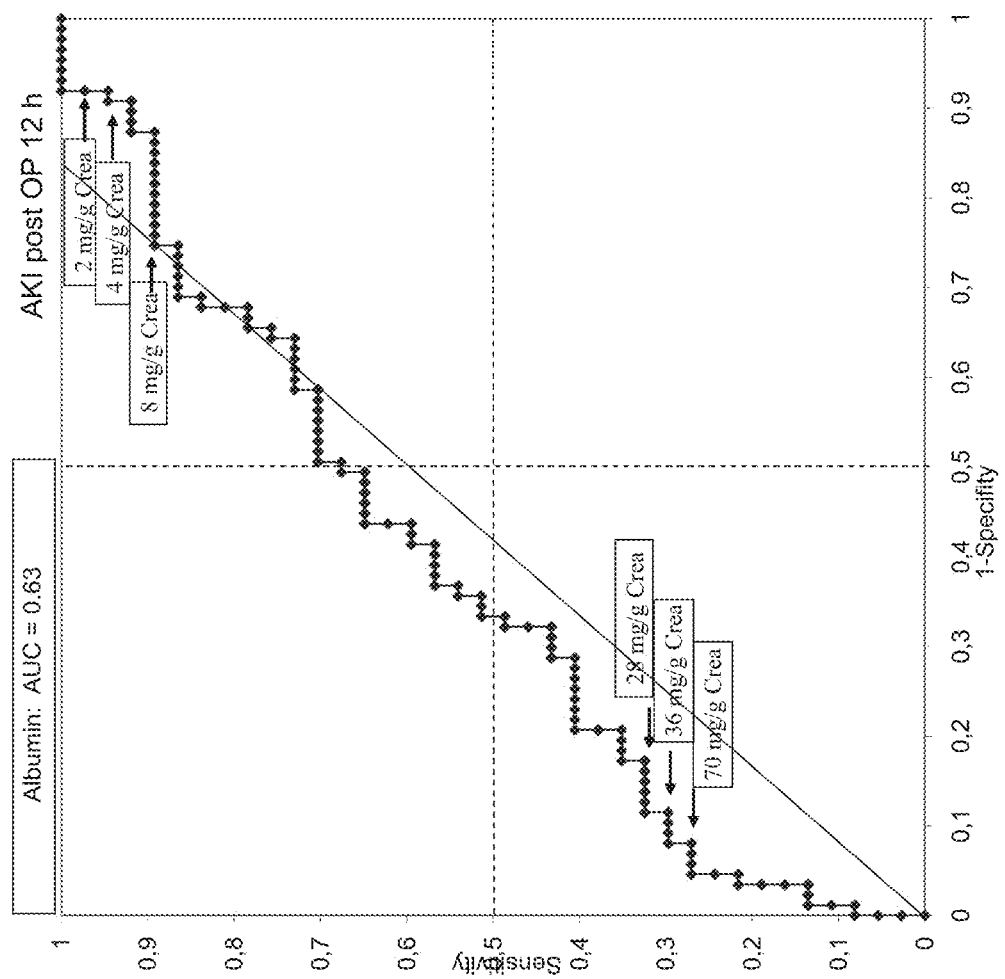
FIG. 10 is a ROC analysis for albumin of samples obtained from the patients described in Example 1 about 12 h after surgery termination, in which analysis was performed with respect to the clinical endpoint acute kidney injury (yes or no).
Figure 11:
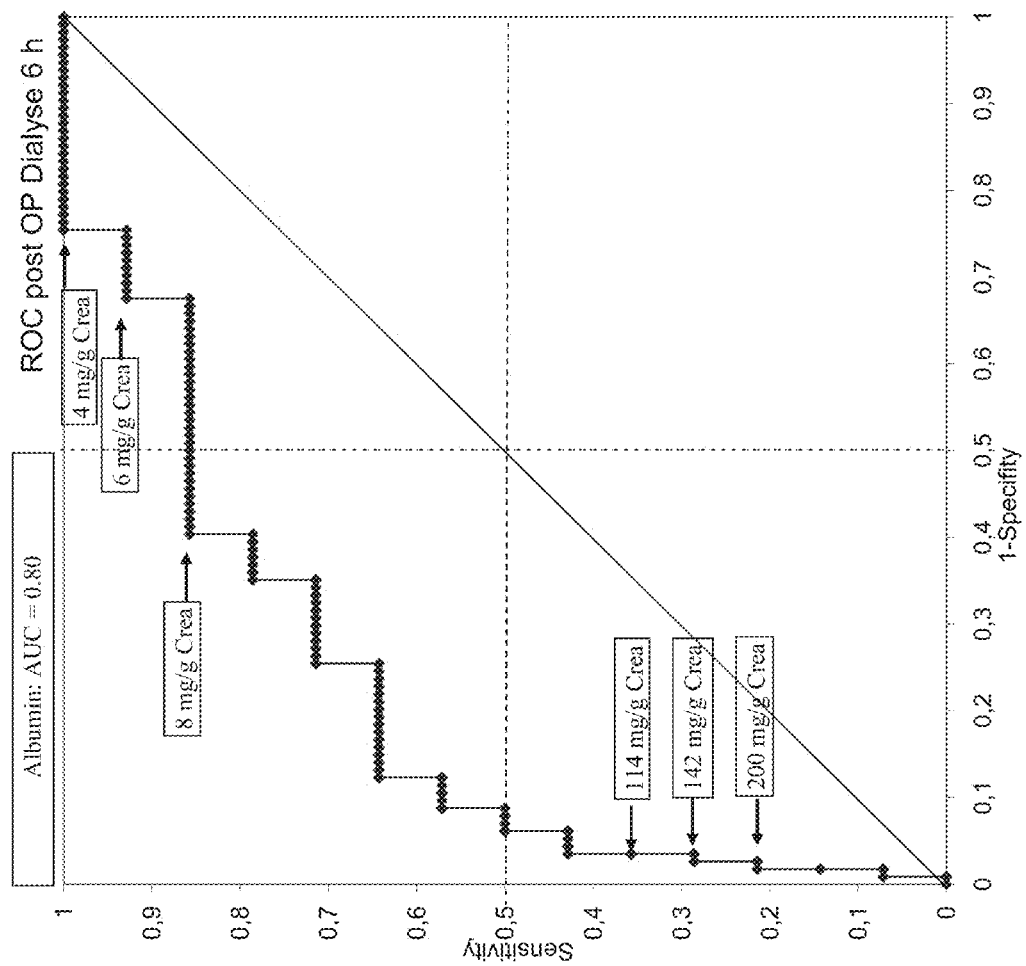
FIG. 11 is a ROC analysis for albumin of samples obtained from the patients described in Example 1 about 6 h after surgery termination, in which analysis was performed with respect to the need for dialysis (yes or no).
Figure 12:
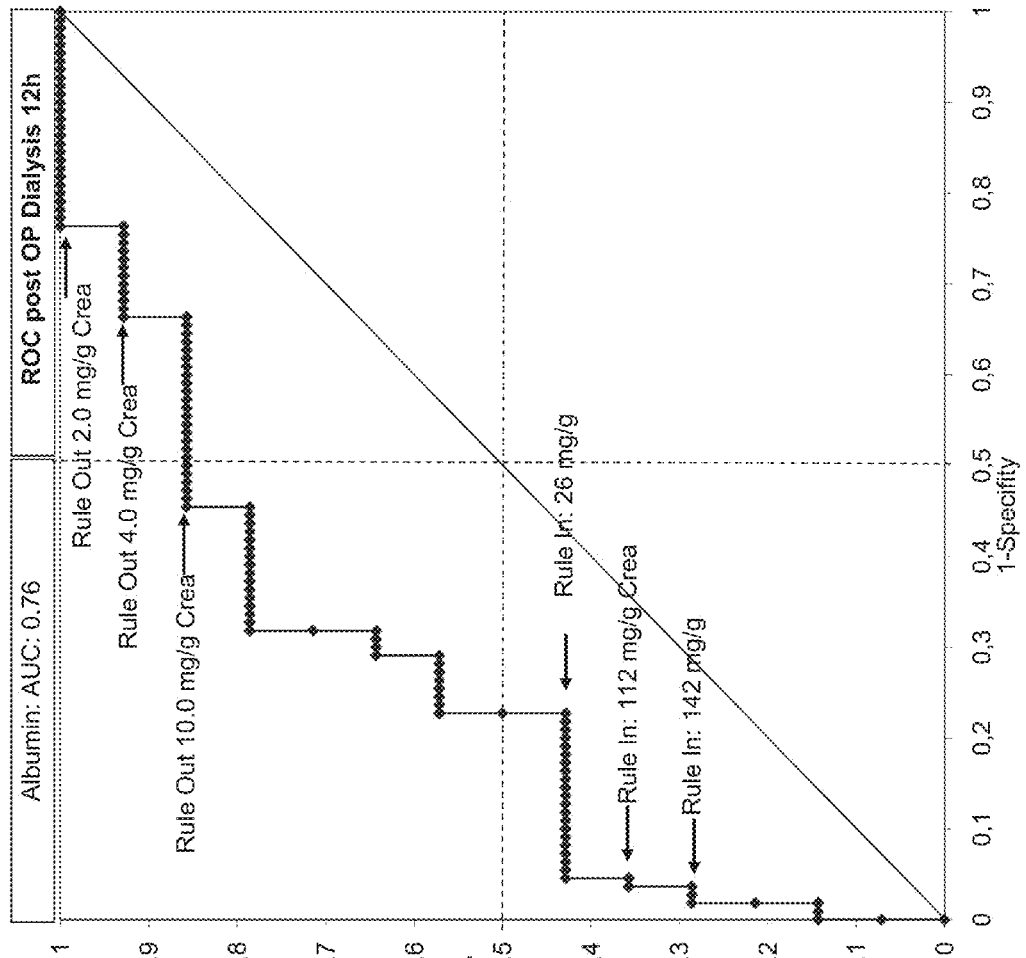
FIG. 12 is a ROC analysis for albumin of samples obtained from the patients described in Example 1 about 12 h after surgery termination, in which analysis was performed with respect to the need for dialysis (yes or no).
Figure 13:
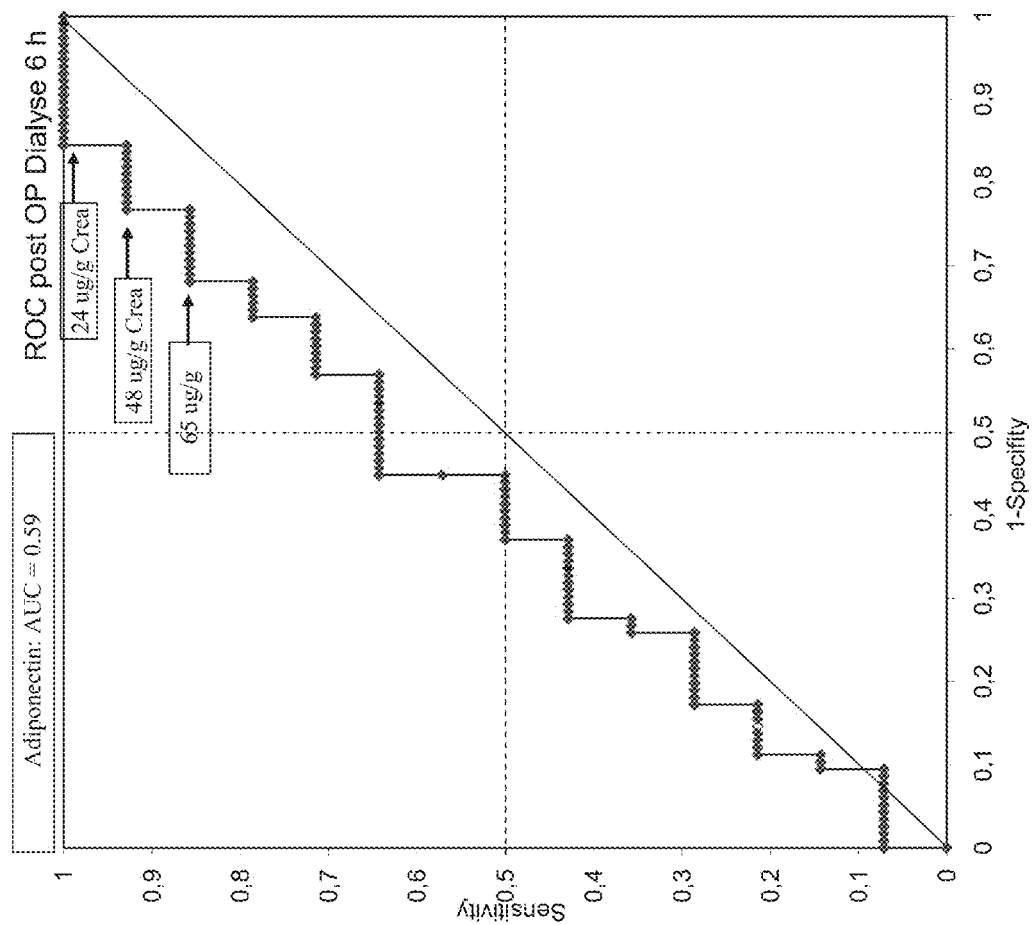
FIG. 13 is a ROC analysis for adiponectin of samples obtained from the patients described in Example 1 about 6 h after surgery termination, in which analysis was performed with respect to the need for dialysis (yes or no)
Figure 14:
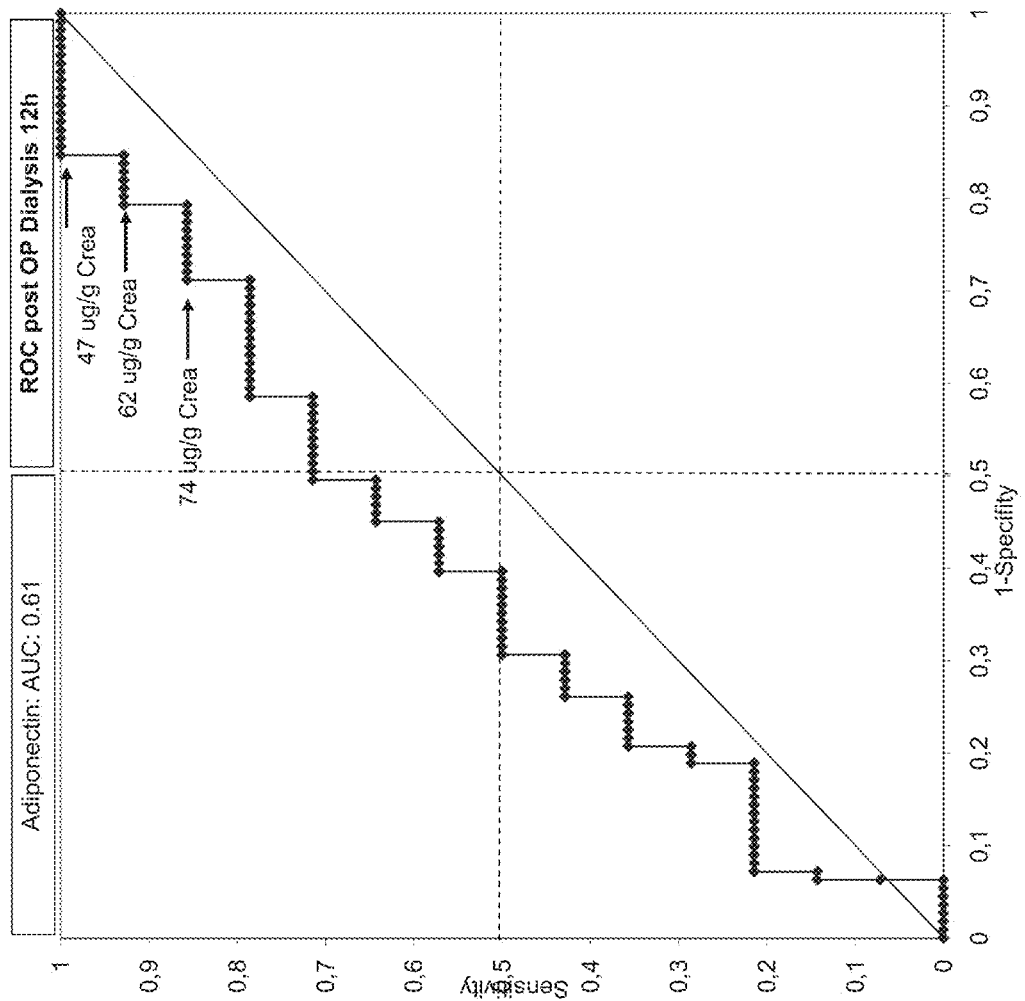
FIG. 14 is a ROC analysis for adiponectin of samples obtained from the patients described in Example 1 about 12 h after surgery termination, in which analysis was performed with respect to the need for dialysis (yes or no).
Figure 15:
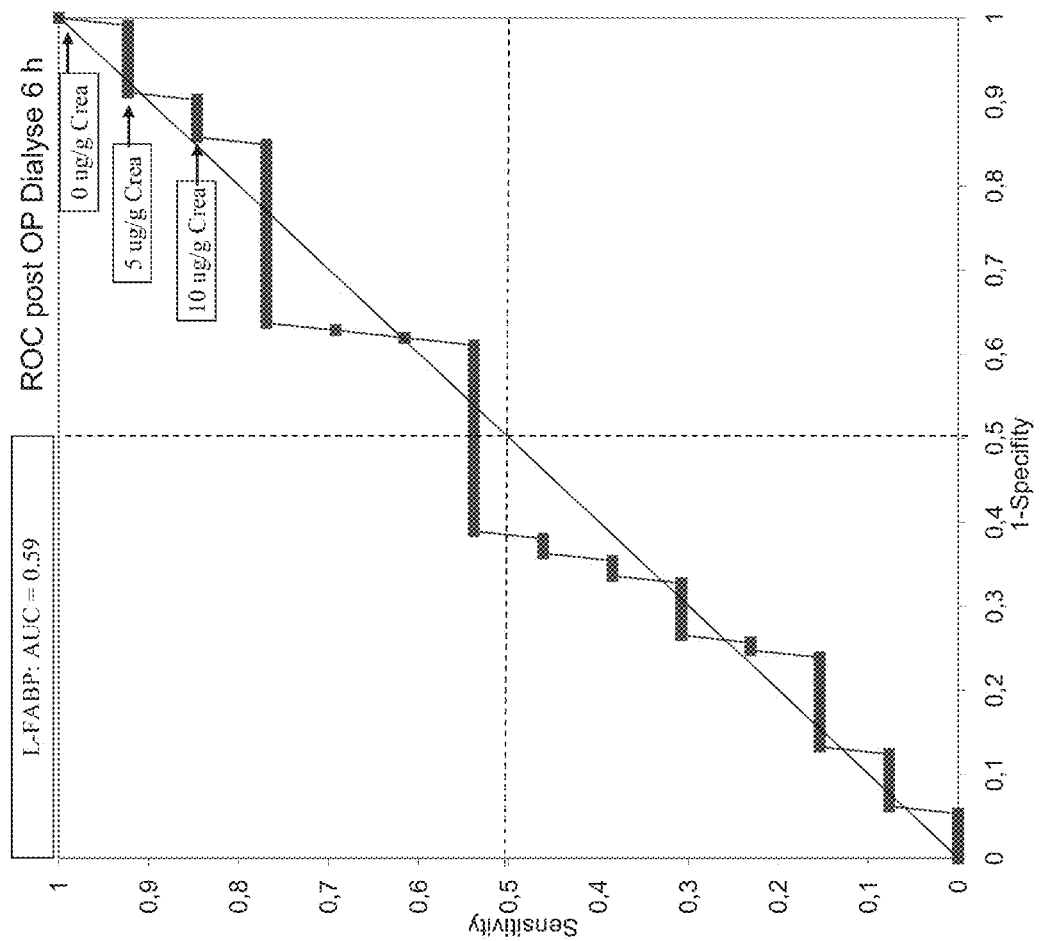
FIG. 15 is a ROC analysis for urinary L-FABP of samples obtained from the patients described in Example 1 about 6 h after surgery termination, in which analysis was performed with respect to the need for dialysis (yes or no).
Figure 16:
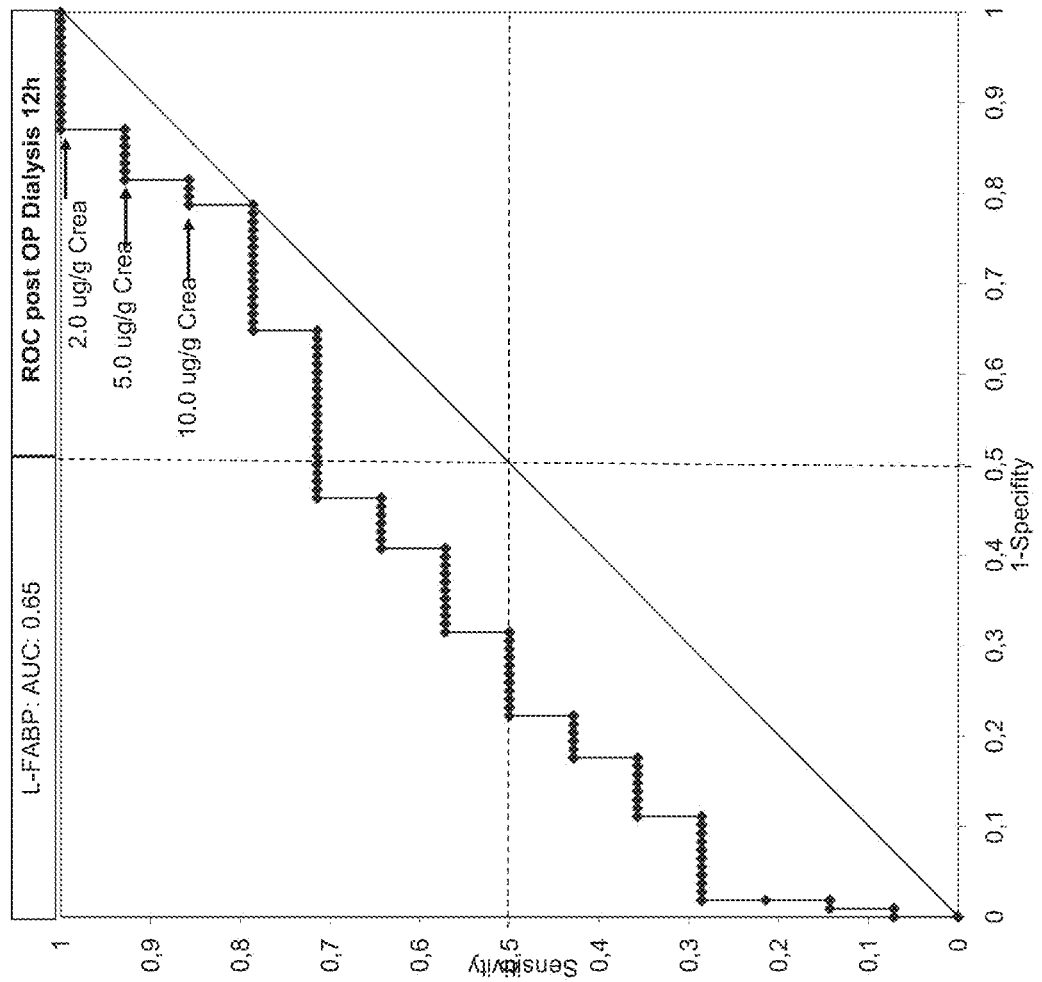
FIG. 16 is a ROC analysis for urinary L-FABP of samples obtained from the patients described in Example 1 about 12 h after surgery termination, in which analysis was performed with respect to the need for dialysis (yes or no).
Figure 17:
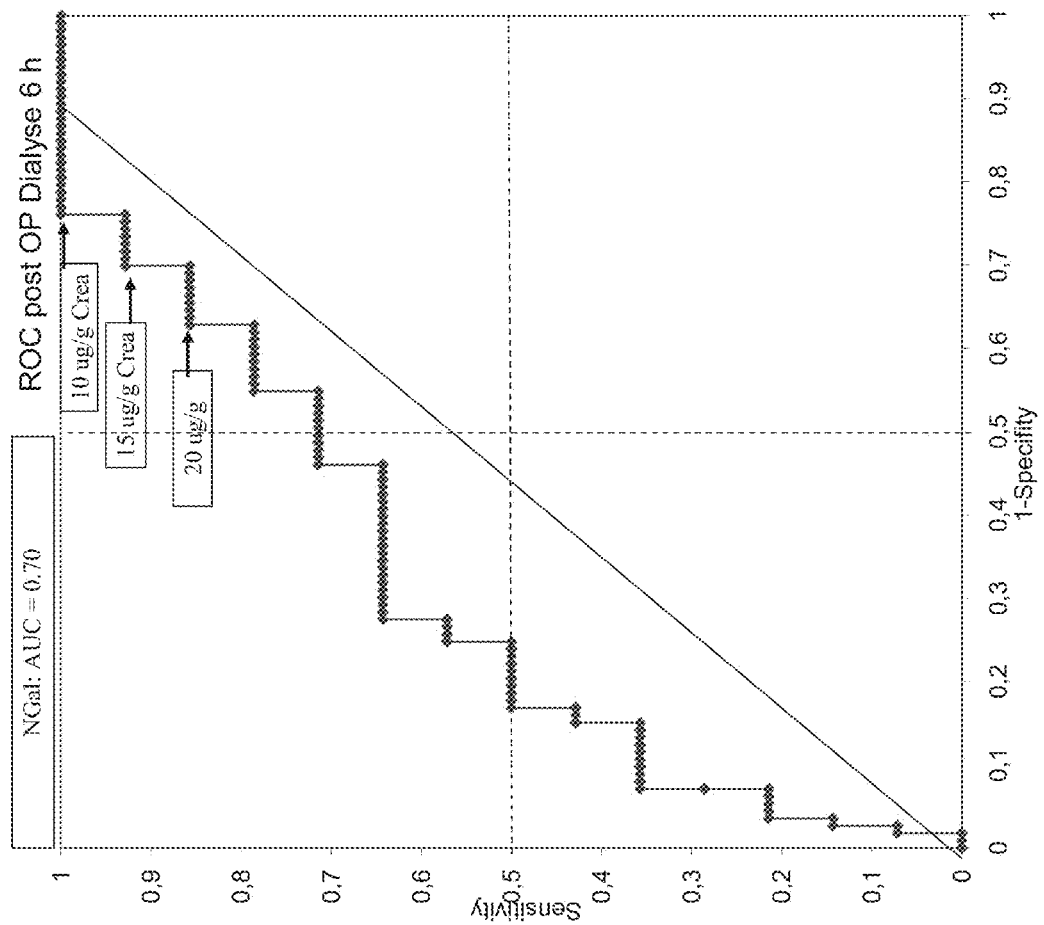
FIG. 17 is a ROC analysis for NGAL of samples obtained from the patients described in Example 1 about 6 h after surgery termination, in which analysis was performed with respect to the need for dialysis (yes or no).
Figure 18:
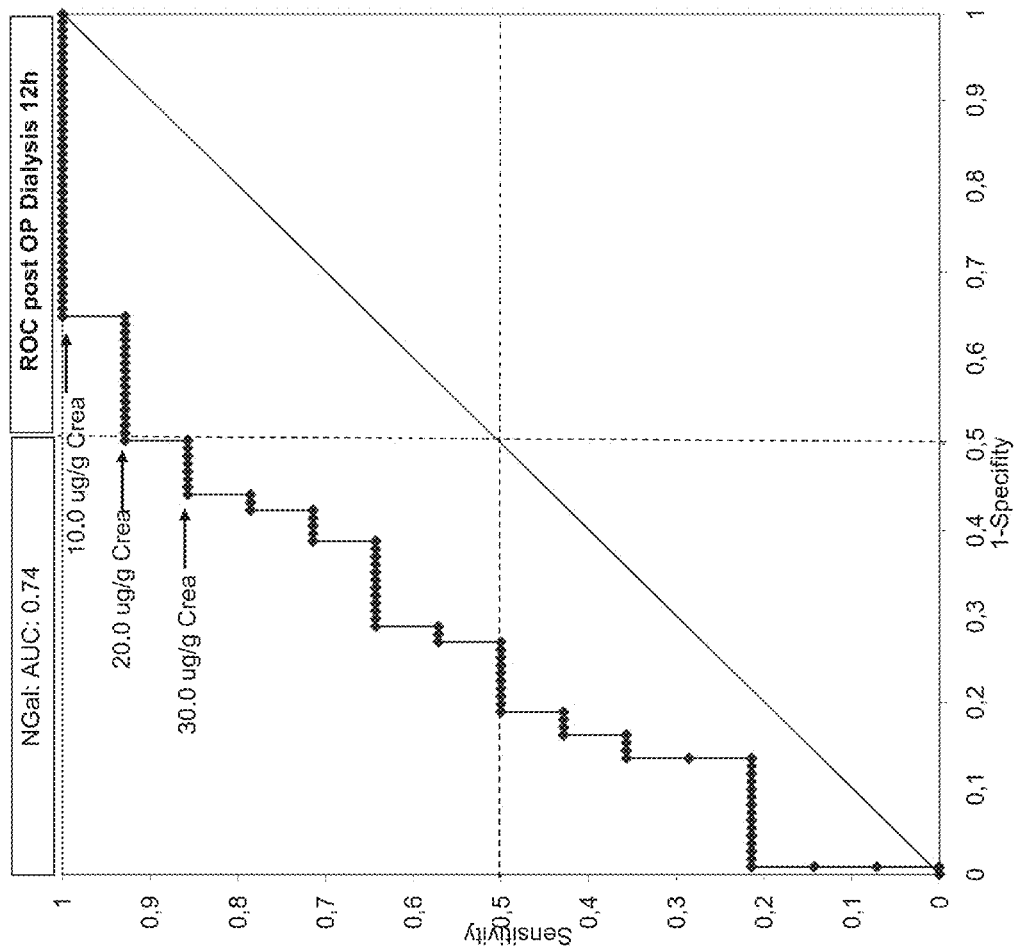
FIG. 18 is a ROC analysis for NGAL of samples obtained from the patients described in Example 1 about 12 h after surgery termination, in which analysis was performed with respect to the need for dialysis (yes or no).

The amount of L-FABP in a sample taken before surgery predicts the need for dialysis after surgery well (see FIG. 2). A sensitivity of approximately 60% can be reached while maintaining a selectivity of about 80%. Thus, the need for dialysis after surgery is correctly predicted for more than half of all patients who finally require dialysis.

It is important to understand that acute kidney injury and specifically acute kidney injury followed by dialysis may be caused by a disease before the intervention or by complications of the intervention itself. In the current study urinary L-FABP identified a subgroup of patients at increased risk of acute kidney injury and dialysis that was not recognized by other kidney functions tests, e.g. based on the determination of creatinine. This identification was possible before the intervention. Risk assessment before the intervention allows taking preventive measures which are not effective or less effective if taken after occurrence of the events leading to acute kidney injury. Such measures include specifically careful fluid balance, avoidance of nephrotoxic drugs and avoidance of low perfusion temperatures if cardiopulmonary bypass is used.

Example 2

A patient is scheduled to undergo cardiovascular bypass grafting. The patient's amount of urinary L-FABP before surgery is 36.0 µg/g Creatinine. Consequently, the fluid balance of the patient is carefully monitored and low perfusion temperatures of the cardiopulmonary bypass are avoided. The patient recovers from surgery without signs or symptoms of kidney injury.

Example 3

A patient is scheduled to undergo cardiovascular bypass grafting. The patient's amount of urinary L-FABP before surgery is 3.1 µg/g Creatinine. Although no special preventive measures are taken, the patient recovers from surgery without signs or symptoms of kidney injury.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of treating a subject who is at risk for an adverse event related to acute kidney injury after cardiovascular bypass surgery, comprising:
   a) detecting full-length liver-type fatty acid binding protein in a first portion of a urine sample of the subject, the sample obtained from the subject prior to the cardiovascular bypass surgery, by contacting, in vitro, the first portion of the urine sample with an antibody that specifically binds to liver-type fatty acid binding protein, wherein the antibody and liver-type fatty acid binding protein form a complex;
   b) quantifying a signal from the complex to obtain an amount of liver-type fatty acid binding protein in the complex;
   c) normalizing the amount of liver-type fatty acid binding protein determined in said step of quantifying to an amount of creatinine;
   d) detecting adiponectin in a second portion of the urine sample of the subject, by contacting, in vitro, the portion of the second sample with an antibody that specifically binds to full-length adiponectin, wherein the antibody and adiponectin form a complex;
   e) quantifying a signal from the complex containing adiponectin to obtain an amount of adiponectin in the complex;
   f) normalizing the amount of adiponectin to an amount of creatinine;
   g) diagnosing the subject as at risk for the adverse event related to acute kidney injury after the cardiovascular bypass surgery when the amount of liver-type fatty acid binding protein is greater than about 10.7 pg liver-type fatty acid binding protein/g creatinine and when the amount of adiponectin is greater than 15.5 pg adiponectin/g creatinine; and
   h) administering a treatment selected from the group consisting of immediate treatment of pulmonary edema and hyperkalemia; dialysis; adjustment of a drug regimen; restriction of water, Na, and K intake; phosphate binders; and sodium polystyrene sulfonate to the subject diagnosed as at risk for the adverse event related to acute kidney injury after the cardiovascular bypass surgery.

2. The method of claim 1, wherein the amount of liver-type fatty acid binding protein in the first portion of the urine sample of the subject is from about 10.8 pg/g creatinine to about 32.3 pg/g creatinine.

* * * * *